(12) United States Patent
Naso et al.

(10) Patent No.: US 7,931,905 B2
(45) Date of Patent: Apr. 26, 2011

(54) CYNOMOLGUS GP80 RECEPTOR AND USES THEREOF

(75) Inventors: Michael Naso, Radnor, PA (US);
Ronald Swanson, San Diego, CA (US);
Bethany Swencki-Underwood, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 0 days.

(21) Appl. No.: 12/469,770

(22) Filed: May 21, 2009

(65) Prior Publication Data

US 2009/0291455 A1 Nov. 26, 2009

Related U.S. Application Data

(60) Provisional application No. 61/055,237, filed on May 22, 2008.

(51) Int. Cl.
*A61K 39/00* (2006.01)
*A61K 39/395* (2006.01)
*C07K 14/00* (2006.01)

(52) U.S. Cl. .................. 424/185.1; 530/350; 424/139.1; 424/143.1; 424/198.1

(58) Field of Classification Search ........................ None
See application file for complete search history.

(56) References Cited

U.S. PATENT DOCUMENTS 5,807,715 A 9/1998 Morrison et al.

OTHER PUBLICATIONS

Yamasaki et al., "Cloning and Expression of the Human Interleukin-6 (BSF-2/IFNβ 2) Receptor," Science 241: 825-828 (1988).
Novick, et al., "Soluble Cytokine Receptors Are Present in Normal Human Urine," Journal of Experimental Medicine, 170: 1409-1414 (1989).
Yasukawa et al., "Purification and Characterization of Soluble Human IL-6 Receptor Expressed in CHO Cells," Journal of Biochemistry, 108: 673-676 (1990).
Kohler et al., "Continuous cultures of fused cells secreting antibody of predefined specificity," Nature, 256: 495-497 (1975).
Queen, et al., "A humanized antibody that binds to the interleukin 2 receptor," Proceedings of the National Academy of Science, USA, 86: 10029-10033 (1989).
Hodgson, et al., "Making Monoclonals in Microbes," Bio/Technology, 9: 421-421 (1991).
Lonberg, et al., "Antigen-specific human antibodies from mice comprising four distinct genetic modifications," Nature, 368: 856-859 (1994).
Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).
Mendez, et al., "Functional transplant of megabase human immunoglobulin loci recapitulates human antibody response in mice," Nature Genetics, 15: 146-156 (1997).
Krebs, et al, "High-throughput generation and engineering of recombinant human antibodies," Journal of Immunological Methods, 254: 67-84 (2001).
Fishwild, et al., "High avidity human IgGκ monoclonal antibodies from a novel strain of minilocus transgenic mice," Nature Biotechnology 14, 845-851 (1996).
Gentz et al., "Bioassay for trans-activation using purified human immunodeficiency virus *tat*-encoded protein: Trans-activation requires mRNA synthesis," Proceedings of the National Academy of Science USA, 86: 821-824 (1989).
Genbank Accession No. XM 001114404, Jun. 14, 2006.

*Primary Examiner* — Robert Landsman
*Assistant Examiner* — Bruce D Hissong
(74) *Attorney, Agent, or Firm* — Eric Dichter

(57) ABSTRACT

Isolated polynucleotides encoding cynomolgus monkey gp80, polypeptides obtainable from expression of these polynucleotides, compositions, recombinant cells, methods of making and using these polynucleotides, polypeptides, and compositions are useful in development of human therapeutics.

9 Claims, 3 Drawing Sheets

CYNOMOLGUS GP80 RECEPTOR AND USES THEREOF

CROSS-REFERENCE TO RELATED APPLICATIONS

This application claims the benefit of U.S. Provisional Application Ser. No. 61/055,237, filed 22 May 2008, the entire contents of which is incorporated herein by reference in its entirety.

FIELD OF THE INVENTION

The present invention relates to the cynomolgus monkey gp80 receptor and uses thereof.

BACKGROUND OF THE INVENTION

IL-6 is a pleiotropic proinflammatory cytokine produced and secreted by a wide variety of cell types, most notably antigen presenting cells, T and B cells. IL-6 is involved in such diverse activities as B cell growth and differentiation, T cell activation, hematopoiesis, osteoclast activation, keratinocyte growth, neuronal growth and hepatocyte activation.

IL-6 plays an important role in B cell abnormalities as demonstrated in systemic lupus erythematosus, multiple myeloma and lymphoproliferative disorders. Similarly, IL-6 is also implicated in the pathogenesis of autoimmune and inflammatory diseases, such as rheumatoid arthritis and osteoarthritis. Evidence also suggests an association between IL-6 and chronic obstructive pulmonary disease and insulin resistance in type 2 diabetes. IL-6 has both pro-inflammatory and anti-inflammatory effects in the immune system, indicating that this cytokine likely plays a central role in regulating the physiological response to disease. Therefore, targeting IL-6 can potentially provide therapeutic benefit in a variety of disease areas.

An increase in the production of IL-6 has been observed in a number of diseases including: Alzheimer's disease, autoimmune diseases, such as rheumatoid arthritis, inflammation, myocardial infarction, Paget's disease, osteoporosis, solid tumors (renal cell carcinoma), prostatic and bladder cancers, neurological cancers, and B-cell malignancies (e.g., Casteleman's disease, certain lymphomas, chronic lymphocytic leukemia, and multiple myeloma). Research has indicated that IL-6 is linked to the pathogenesis of many of these diseases, particularly, cancer and, therefore, blocking IL-6 should translate into clinical benefits.

IL-6 induces signaling through a cell surface heterodimeric receptor complex composed of a ligand binding subunit (gp80) and a signal transducing subunit (gp130). IL-6 is able to bind gp80, but does not bind to gp130 unless in the presence of gp80.

The cDNA for human gp80 has been isolated (Yamasaki et al., 1988, Science 241), and was found to be 1407 bp in length. Human gp80 cDNA encodes a 468 amino acid protein, having a 19 amino acid signal peptide and a domain of approximately 90 amino acids that is similar to a domain in the immunoglobulin superfamily. The cytoplasmic domain of approximately 82 amino acids lacks a tyrosine/kinase domain, unlike other growth factor receptors. The mature human protein has a calculated molecular weight of 51.6 kDa. A soluble form of gp80 has been reported (Novick et al., 1989, J. Exp. Med. 170) which arises from proteolytic cleavage of membrane-bound gp80. This soluble receptor has been shown to bind to IL-6 in solution (Yasukawa et al., 1990, J. Biochem. 108)

Extensive safety testing is required for an IL-6 or gp80 (IL-6R) human therapeutic to be brought to the marketplace. Such safety testing involves both in vivo safety testing in animal models as well as the in vitro testing of these therapeutics. For example, antibody based IL-6 and gp80 therapeutics may require the generation of surrogate antibodies against an IL-6 or gp80 peptide chain expressed by a particular model animal as well as significant in vitro characterization of such surrogate antibodies. Such surrogate generation and in vitro characterization may require the use of IL-6 and gp80 polynucleotides and peptide chains from a suitable model animal. Importantly, the identification of suitable animal models for such safety testing requires the identification of animal species capable of expressing a gp80 with high identity and homology to human gp80 (SEQ ID NO:11).

Thus, a need exists for the identification of polynucleotides encoding gp80s and gp80 peptide chains capable of being expressed in an animal model suitable for the safety testing of IL-6 and gp80 therapeutics. A need also exists for related methods such as methods of expressing peptide chains and testing the safety of an IL-6 or gp80 therapeutic in an animal model identified as suitable for safety assessment of IL-6 or gp80 therapeutics.

SUMMARY OF THE INVENTION

Figure 1:
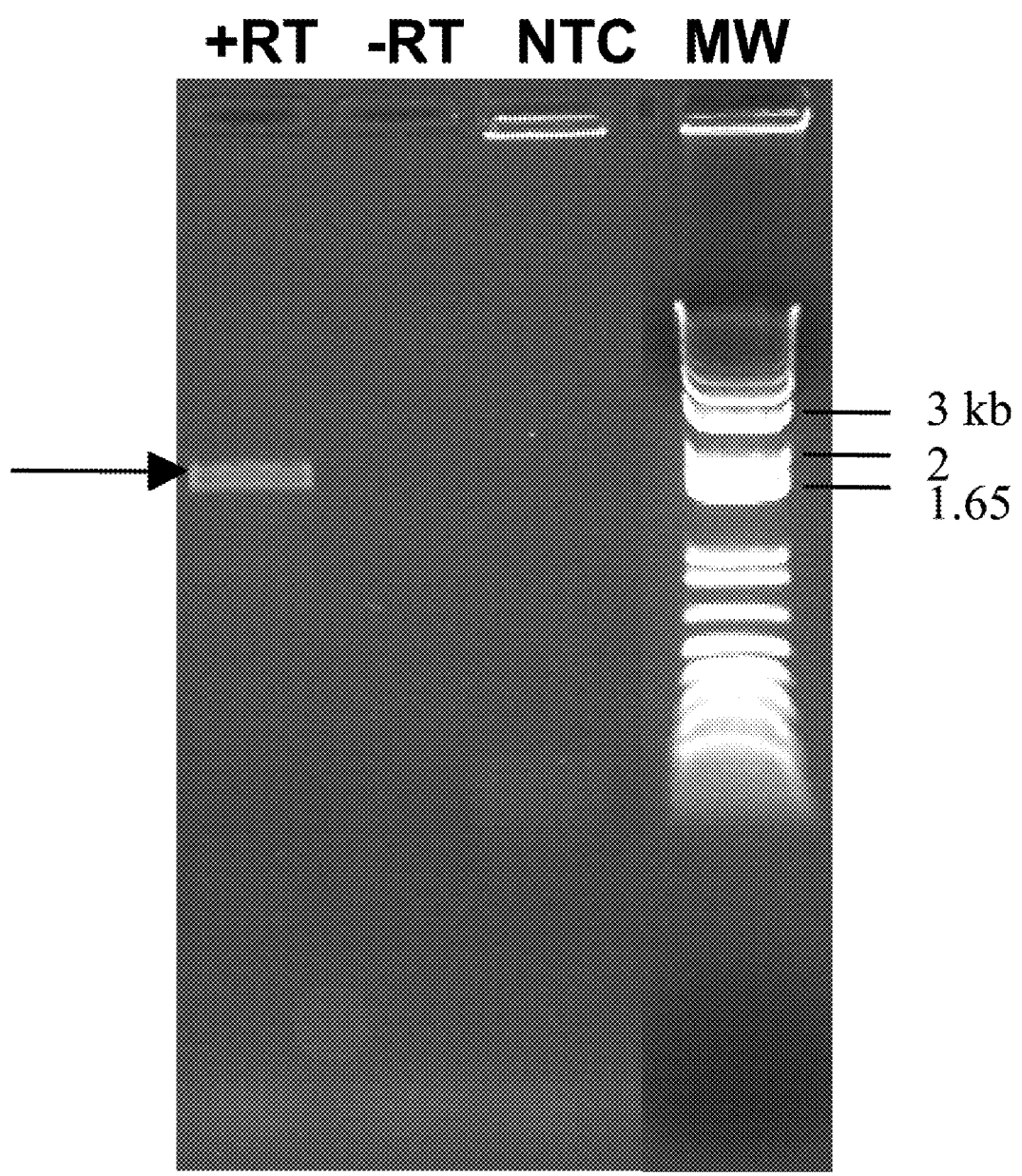
FIG. 1 is a depiction of a gel showing RT-PCR products separated by agarose gel electrophoresis and visualized under UV light, including a band for cyno gp80.

One aspect of the invention is an isolated polynucleotide comprising a polynucleotide encoding cyno gp80 having the sequence shown in SEQ ID NO:1 or a complementary sequence thereof. Another aspect of the invention is an isolated polynucleotide comprising a polynucleotide encoding the extracellular domain of cyno gp80 having the sequence shown in SEQ ID NO:5 or a complementary sequence thereof.

Another aspect of the invention is a vector comprising an isolated polynucleotide having the sequence shown in SEQ ID NOS:1 or 5.

Another aspect of the invention is a polypeptide comprising a peptide chain having the mature, full-length cyno gp80 sequence set forth in SEQ ID NO:2. Yet another aspect of the invention is a polypeptide comprising a peptide chain having his-tagged, mature, full-length cyno gp80 sequence set forth in SEQ ID NO:4. A further aspect of the invention is a polypeptide comprising a peptide chain having the extracellular domain of mature cyno gp80 sequence set forth in SEQ ID NO:6. An additional aspect of the invention is a polypeptide comprising a peptide chain having the his-tagged extracellular domain of mature cyno gp80 sequence set forth in SEQ ID NO:8. Also included in the invention is a polypeptide comprising a peptide chain having the mature cyno gp80 sequence set forth in SEQ ID NO:10 without the signal sequence.

Another aspect of the invention is a method for expressing a peptide chain comprising the steps of providing a DNA or RNA sequence coding for a polypeptide comprising the sequence set forth in SEQ ID NOS:2, 6, or 10; providing the components of a cell free expression system; initiating cell free expression from the RNA provided; recovering the peptide chain; and confirming expression of at least one peptide chain comprising the sequence set forth in SEQ ID NOS:2, 6, or 10.

Another aspect of the invention is a method for determining if a gp80 therapeutic causes adverse events comprising providing a gp80 therapeutic, a first cynomolgus monkey, and a second cynomolgus monkey; administering the gp80 therapeutic to the first cynomolgus monkey; and determining whether the first cynomolgus monkey is presenting a deleterious symptom relative to the second monkey, where presentation of a deleterious symptom by the first cynomolgus monkey shows the gp80 therapeutic is unsafe and a lack of presentation of a deleterious symptom by the first cynomolgus monkey shows the gp80 therapeutic is safe.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The present invention provides isolated cynomolgus monkey (*Macaca fascicularis*) ("cyno") gp80 polynucleotides, vectors comprising these polynucleotides, isolated host cells, peptide chains obtainable from expression of these polynucleotides, methods for expressing the peptide chains of the invention, and uses of these are disclosed.

Importantly, the full-length cyno gp80 peptide chain sequence (SEQ ID NO:2) is 97% identical, and 96.8% similar to the human gp80 (IL-6R) peptide chain (SEQ ID NO:11).

The compositions and methods of the invention can be used for a variety of specific applications. The polynucleotides and vectors of the invention are useful because they encode cynomolgus monkey gp80 peptide chains and can be used to express these peptide chains. These cyno gp80 peptide chains are, in turn, useful because they can be used to increase or control inflammatory responses after exposure to dsRNA or other gp80 ligands when they are recombinantly over expressed or introduced by other means into a host animal or tissue.

Peptide chains comprising the extracellular domain of cyno gp80 can also be used as ligand sink type antagonists that bind available gp80 ligands or gp80 associated proteins necessary for gp80 activation and thus control gp80 or IL-6-related activity. Cyno gp80 peptide chains can also be used to generate therapeutic antibodies for the positive or negative modulation of the activity of cyno gp80 or gp80s from other sources. This is desirable because agonist therapeutic antibodies can be used to increase activation of cyno gp80 or other gp80s to help control inflammatory responses while antagonist therapeutic antibodies can be used to decrease activation of cyno gp80 or other gp80s to help control conditions associated with gp80 receptor activation mediated inflammatory responses. Cyno gp80 peptide chains can also be used in in vitro or in vivo assays to identify other therapeutics, such as small molecules and non-antibody biological therapeutics (e.g., catalytic proteins) capable of modulating the activity of cyno gp80 or other gp80s. The methods of expression disclosed are useful because these methods permit the expression of cyno gp80 peptides. Other methods disclosed are useful because they permit a safety assessment of a gp80 therapeutic.

The term "polynucleotide" means a molecule comprising a chain of nucleobases covalently linked by a sugar-phosphate backbone or other equivalent covalent chemistry. Double and single stranded DNAs and RNAs are typical examples of polynucleotides.

The term "complementary sequence" means a second isolated polynucleotide sequence that is antiparallel to a first isolated polynucleotide sequence and that comprises nucleobases complementary to the nucleobases in the first polynucleotide sequence. Typically, such "complementary sequences" are capable of forming a double stranded polynucleotide molecule such as double stranded DNA or double stranded RNA when combined under appropriate conditions with the first isolated polynucleotide sequence.

The term "vector" means a polynucleotide capable of being duplicated within a biological system or that can be moved between such systems. Vector polynucleotides typically contain elements, such as origins of replication or selection markers, that function to facilitate the duplication or maintenance of these polynucleotides in a biological system. Examples of such biological systems may include cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a peptide chain encoded by a polynucleotide sequence present in the expression vector.

The term "peptide chain" means a molecule that comprises at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "antibody" means immunoglobulin or antibody molecules comprising polyclonal antibodies, monoclonal antibodies including murine, human, humanized and chimeric monoclonal antibodies and antibody fragments, portions, or variants. Antibodies are secreted proteins constitutively expressed and secreted by plasma cells. Antibodies may be of any isotype such as IgG, IgA, or IgM and may comprise antibody fragments such as Fab' fragments. An antibody may also be a bispecific antibody that specifically binds two different peptide chain epitopes.

Antibodies can be produced using plasma cells immortalized by standard methods such as hybridoma generation or by transfection of antibody heavy and/or light chain genes into an immortalized B cell, such as a myeloma cell or other cell types, such as Chinese hamster ovary (CHO) cells, plant cells and insect cells.

The term "monoclonal antibody" (mAb) as used herein means an antibody (or antibody fragment, such as a Fab, single domain antibody, etc.) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., 256 Nature 495 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 5,807,715. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., 86 Proc. Natl. Acad. Sci. (USA) 10029 (1989) and Hodgson et al., 9 Bio/Technology 421 (1991).

Exemplary human framework sequences useful for humanization are disclosed at, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www. biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www. ibt.unam.mx/vir/V_mice.html; http://www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; and Kabat et al., Sequences of Proteins of Immunological Interest, U.S. Dept. Health (1987), each entirely incorporated herein by reference.

Fully human mAbs lacking any non-human sequences can be prepared from human immunoglobulin transgenic mice by techniques referenced in, e.g., Lonberg et al., 368 Nature 856 (1994); Fishwild et al., 14 Nature Biotech. 845 (1996) and Mendez et al., 15 Nature Genetics 146 (1997). Human mAbs can also be prepared and optimized from phage display libraries by techniques referenced in, e.g., Knappik et al., 296 J. Mol. Biol. 57 (2000) and Krebs et al., 254 J. Immunol. Meth. 67 (2001).

An antibody molecule or preparation "specifically binds" a given antigen when it binds this antigen with higher affinity and in a specific, as opposed to non-specific fashion, relative to a second non-identical antigen. Stated differently, the "specific binding" of an antibody molecule or preparation can be used to distinguish between two different peptide chains.

A "fragment" is a peptide chain having an amino acid sequence that comprises a portion, but not all, of any amino acid sequence of any peptide chain of the invention. Fragments can include, for example, truncated peptide chain having a portion of an amino acid sequence corresponding to a signal peptide, extracellular domain, transmembrane domain, or cytoplasmic domain, or variants thereof, such as a continuous series of residues that includes a heterologous amino- and/or carboxy-terminal amino acid sequence. Degradation forms of the peptide chains of the invention produced by, or in, a host cell are also included. Other exemplary fragments are characterized by structural or functional attributes such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions and high antigenic index regions. Importantly, the peptide chains of the invention can be used or provided as fragments.

A "variant peptide chain" is a second peptide chain in which amino acid substitutions, insertions, deletions or combinations thereof have been made relative to a first peptide chain. Naturally occurring, modified or atypical amino acids can be used for substitutions and insertions.

A "variant polynucleotide" is a second polynucleotide in which nucleic acid residue substitutions, insertions, deletions, or combinations thereof have been made relative to a first polynucleotide sequence. Naturally occurring or modified nucleobases can be used for substitutions and deletions. The various polynucleotides encoding the amino acid sequence set forth in SEQ ID NOS:2, 4, 6, 8 and 10 are additional exemplary variant polynucleotides relative to the polynucleotide having the nucleotide sequences set forth in SEQ ID NOS:1, 3, 5, and 7.

The term "gp80 therapeutic" means a molecule or preparation that is believed to provide a therapeutic benefit and is believed to provide that therapeutic benefit, in part, through the activity of a gp80. Such gp80s may comprise the peptide chains of the invention or be generated using the peptide chains of the invention. Examples of gp80 therapeutics include cyno gp80 agonists, antibodies or other antagonists to cyno gp80, known cyno gp80 ligands, such as IL-6, that produce the therapeutic benefits of increased anti-inflammatory activity and the like.

The term "deleterious symptom" means any symptom presented by an animal that indicates harm to the animal has occurred.

One aspect of the invention is an isolated polynucleotide comprising a polynucleotide having the sequence set forth in SEQ ID NOS:1, 3, 5, or 7 or a complementary sequence thereof. The polynucleotide sequences set forth in SEQ ID NOS: 1, 3, 5, and 7 encode peptide chain comprising the predicted mature form of cyno gp80, the his-tagged mature form, extracellular domain of cyno gp80 and his-tagged extracellular domain.

The polynucleotides of the invention may be produced by chemical synthesis, such as solid phase polynucleotide synthesis on an automated polynucleotide synthesizer. Alternatively, the polynucleotides of the invention may be produced by other techniques, such as PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide, as described in Gentz et al., 86 *Proc. Natl. Acad. Sci. (USA)* 821 (1989) or the HA peptide tag as described in Wilson et al., 37 *Cell* 767 (1984) which facilitate the purification of fused polypeptides.

Figure 2:
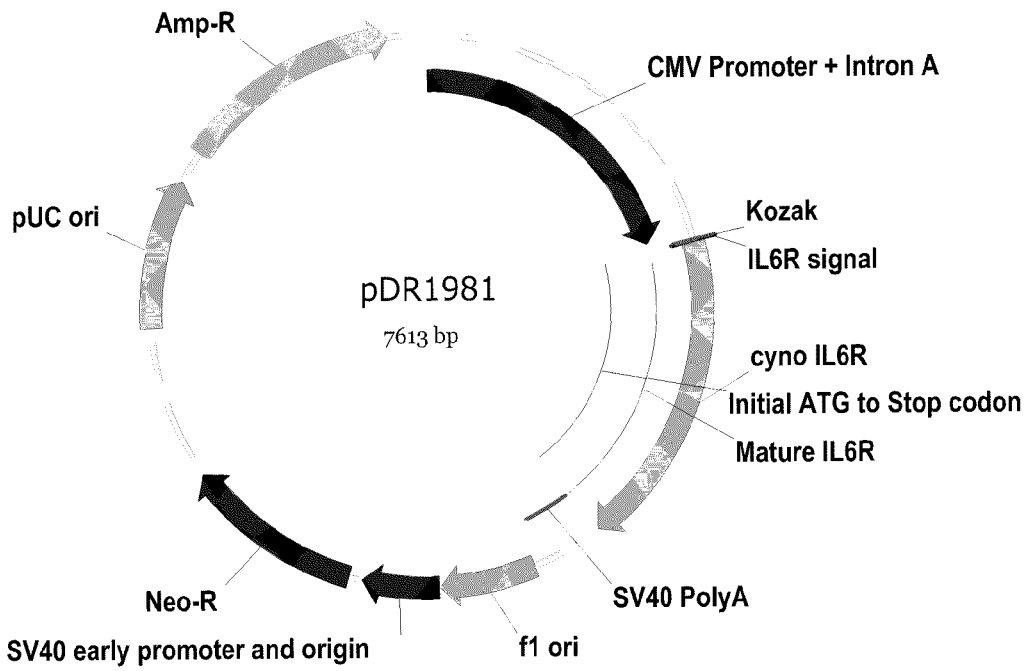
FIG. 2 is a vector map of the polynucleotide (SEQ ID NO:1) encoding the full-length mature cyno gp80 peptide chain.
Figure 3:
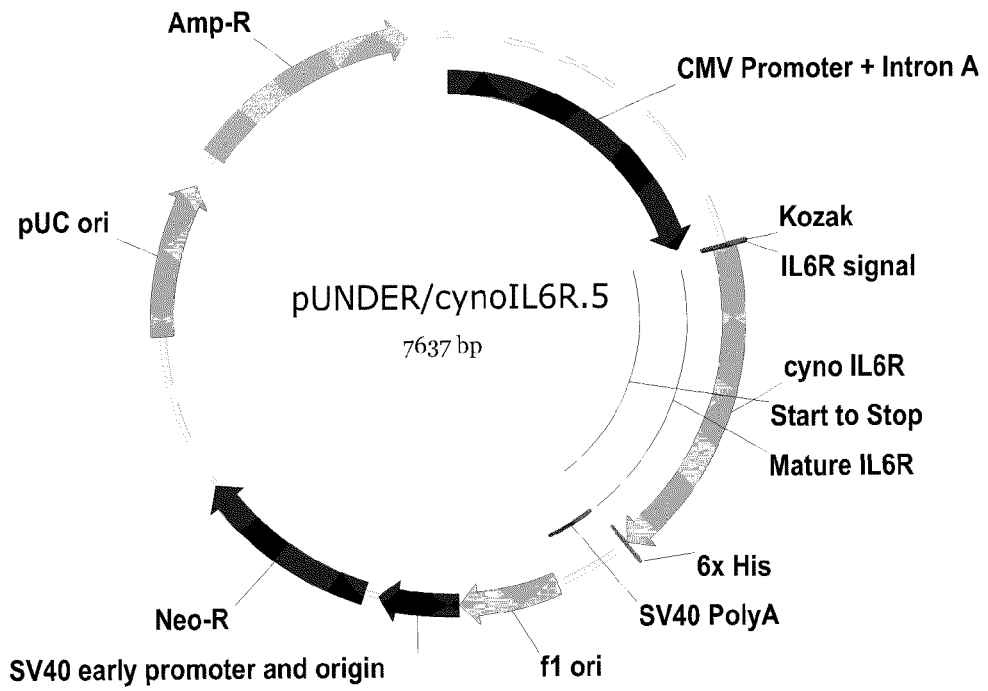
FIG. 3 is a vector map of the polynucleotide (SEQ ID NO:3) encoding the his-tagged full-length mature cyno gp80 peptide chain.

The present invention also includes vectors comprising an isolated polynucleotide having the sequence set forth in SEQ ID NOS:1, 3, 5, and 7. Expression vector maps including SEQ ID NO:1, encoding SEQ ID NO:2, and including SEQ ID NO:3, encoding SEQ ID NO:4, the his-tagged cyno gp80, are shown in FIGS. 2 and 3, respectively. The vector shown in FIG. 2 is a polynucleotide (DNA) expression vector designated pDR1981 that encodes a peptide chain comprising full-length cyno gp80 (SEQ ID NO:2). The vector shown in FIG. 3 is a polynucleotide (DNA) expression vector designated pUNDER/cynoIL6R.5 that encodes a peptide chain comprising the his-tagged full-length cyno gp80 (SEQ ID NO:2). The His tag is 6x with G-S residues inserted between the gp80 sequence and tag during cloning.

Figure 4:
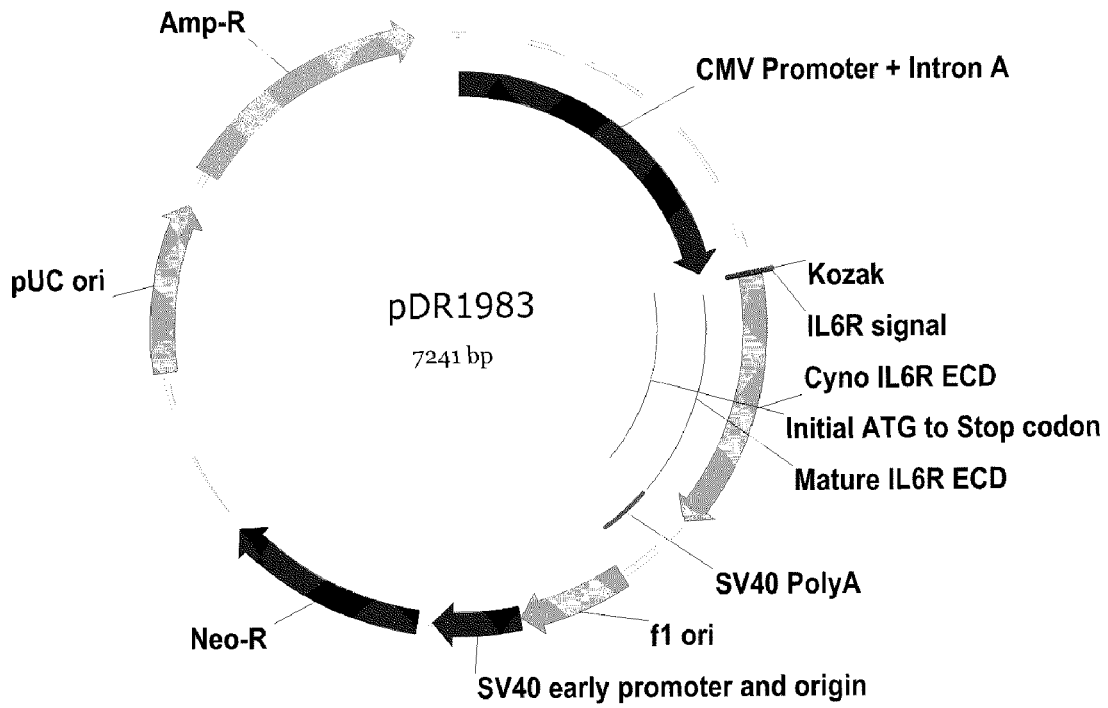
FIG. 4 is a vector map of the polynucleotide (SEQ ID NO:5) encoding the extracellular domain of the mature cyno gp80 peptide chain.
Figure 5:
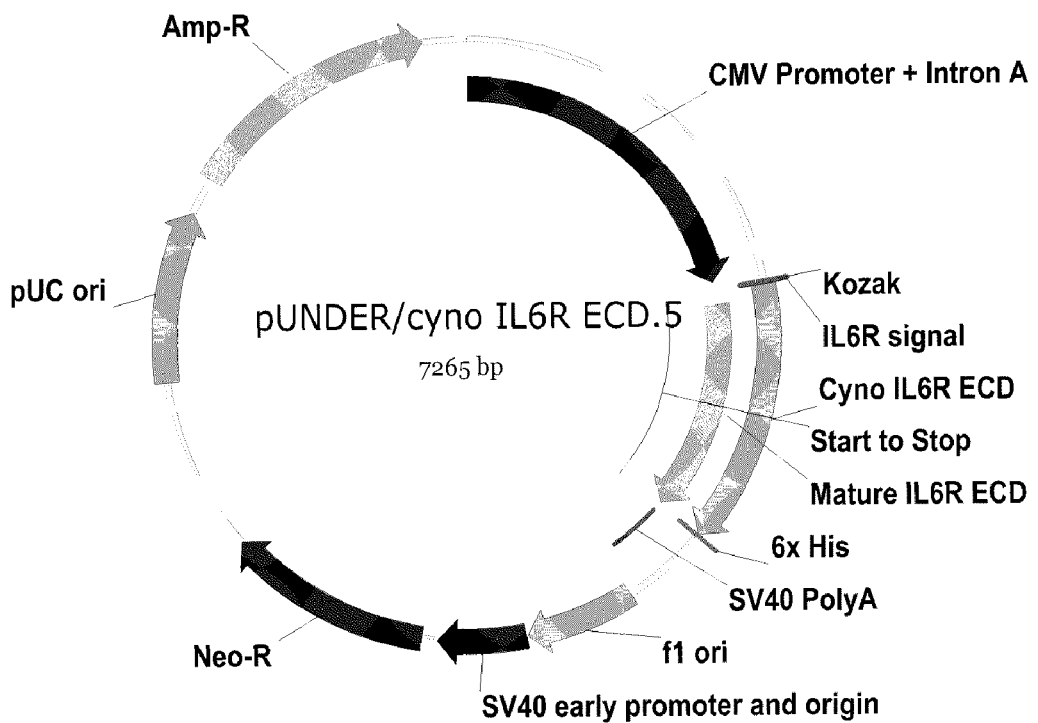
FIG. 5 is a vector map of the polynucleotide (SEQ ID NO:7) encoding the his-tagged extracellular domain of the mature cyno gp80 peptide chain.

Expression vector maps including SEQ ID NO:5, encoding SEQ ID NO:6, the extracellular domain of cyno gp80, and including SEQ ID NO:7, encoding SEQ ID NO:8, the his-tagged extracellular domain of cyno gp80, are shown in FIGS. 4 and 5, respectively. The vector shown in FIG. 4 is a polynucleotide (DNA) expression vector designated pDR1983. The vector shown in FIG. 5 is a polynucleotide (DNA) expression vector designated pUNDER/cynoIL6R ECD.5. The His tag is 6x with G-S residues inserted between the gp80 sequence and tag during cloning.

The vectors of the invention are useful for maintaining polynucleotides, duplicating polynucleotides, or driving expression of a peptide chain encoded by a vector of the invention in a biological systems—including reconstituted biological systems.

Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids.

The vectors of the invention can be formulated in microparticles, with adjuvants, with lipid, buffer or other excipients as appropriate for a particular application.

In one embodiment of the invention the vector is an expression vector.

Expression vectors typically comprise nucleic acid sequence elements that can control, regulate, cause or permit expression of a peptide chain encoded by such a vector. Such elements may comprise transcriptional enhancer binding sites, RNA polymerase initiation sites, ribosome binding sites, and other sites that facilitate the expression of encoded peptide chains in a given expression system. Such expression systems may be cell based, or cell free systems well known in the art. Nucleic acid sequence elements and parent vector sequences suitable for use in the expression of encoded peptide chains are also well known in the art.

Another embodiment of the invention is an isolated host cell comprising a vector of the invention.

An exemplary plasmid derived expression vector useful for expression of the polypeptides of the invention comprises an *E. coli* origin of replication, an aph(3')-1a kanamycin resistance gene, HCMV immediate early promoter with intron A, a synthetic polyA sequence and a bovine growth hormone terminator. Another exemplary plasmid derived expression vector comprises an *E. coli* origin of replication, an ant(4')-1a kanamycin resistance gene, Rous sarcoma virus long terminal repeat sequences, HCMV immediate early promoter and an SV40 late polyA sequence.

Representative host cell examples include Archaea cells; bacterial cells such as *Streptococci, Staphylococci, Enterococci, E. coli, Streptomyces,* cyanobacteria, *B. subtilis* and *S. aureus*; fungal cells such as *Kluveromyces, Saccharomyces,* Basidomycete, *Candida albicans* or *Aspergillus*; insect cells such as *Drosophila* S2 and Spodoptera Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art from laboratory manuals such as Davis et al., *Basic Methods in Molecular Biology*, $2^{nd}$ ed., Appleton & Lange, Norwalk, Conn. (1994) and Sambrook et al., *Molecular Cloning: A Laboratory Manual*, $3^d$ ed., Cold Spring Harbor Laboratory Press, Cold Spring Harbor, N.Y. (2001). These methods include calcium phosphate transfection, DEAE-Dextran mediated transfection, microinjection, cationic lipid-mediated transfection, electroporation, transduction, scrape loading, ballistic introduction and infection.

The present invention comprises an isolated peptide chain having the sequence set forth in SEQ ID NO:2. SEQ ID NO:2 is a peptide chain comprising the predicted mature form of cyno gp80. The present invention also comprises an isolated peptide chain comprising a peptide chain having the sequence set forth in SEQ ID NO:4. SEQ ID NO:4 is a peptide chain comprising the His-tagged predicted mature form of cyno gp80.

The present invention comprises an isolated peptide chain having the sequence set forth in SEQ ID NO:6. SEQ ID NO:6 is a peptide chain comprising the predicted extracellular domain of the mature form of cyno gp80. The present invention also comprises an isolated peptide chain comprising a peptide chain having the sequence set forth in SEQ ID NO:8. SEQ ID NO:8 is a peptide chain comprising the His-tagged extracellular domain of the predicted mature form of cyno gp80. The present invention further comprises an isolated peptide chain comprising a peptide chain having the sequence set forth in SEQ ID NO:10. SEQ ID NO:10 is a peptide chain comprising the predicted mature form of cyno gp80 without the 19-amino acid signal sequence.

The peptide chains of the invention may be produced by chemical synthesis, such as solid phase peptide syntheses, on an automated peptide synthesizer. Alternatively, the peptide chains of the invention can be obtained from polynucleotides encoding these peptide chains by the use of cell free expression systems such as reticulocyte lystate based expression systems, wheat germ extract based expression systems, and *Escherichia coli* extract based expression systems. The peptide chains of the invention can also be obtained by expression and isolation from cells harboring a nucleic acid sequence of the invention by techniques well known in the art, such as recombinant expression of easily isolated affinity labeled peptide chains. Those skilled in the art will recognize other techniques for obtaining the peptide chains of the invention.

The peptide chains of the invention may comprise fusion peptide chains comprising a peptide chain of the invention fused with second peptide chain. Such second peptide chains may be leader or secretory signal sequences, a pre- or pro- or prepro-protein sequence, as well as naturally occurring, or partially synthetic sequences derived in part from a naturally occurring sequence or an entirely synthetic sequence. Secretory signal or leader peptide chain sequences may be selected to direct secretion of the peptide chains of the invention into the lumen of the endoplasmic reticulum or extracellular environment; such peptide chain sequences may be heterologous or endogenous to any peptide chain from a cynomolgus monkey or comprise hybrids of these.

The peptide chains of the invention can also be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the peptide chains of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected.

The peptide chains and nucleic acids of the invention can also be provided in the form of a pharmaceutical preparation, such as a vaccine for eliciting an immune response, that can be provided in unit dose forms. The appropriate therapeutically effective dose can be determined readily by those of skill in the art. A determined dose may, if necessary, be repeated at appropriate time intervals selected as appropriate by a physician or other person skilled in the relevant art (e.g., nurse, veterinarian, or veterinary technician) during the treatment period.

The peptide chains of the invention can be lyophilized for storage and reconstituted in a suitable carrier prior to use. This technique has been shown to be effective with conventional protein preparations. Lyophilization and reconstitution techniques are well known in the art.

Another embodiment of the invention is a method for expressing a peptide chain comprising the steps of providing a host cell of the invention; culturing the host cell under conditions sufficient for the expression of at least one peptide chain comprising the sequence set forth in SEQ ID NOS:2, 4, 6, 8, or 10; recovering the peptide chain; and, optionally, confirming expression of at least one peptide chain comprising the sequence set forth in SEQ ID NOS:2, 4, 6, 8, or 10.

Host cells can be cultured under any conditions suitable for maintaining or propagating a given type of host cell and sufficient for expressing a peptide chain. Culture conditions, media, and related methods sufficient for the expression of peptide chains are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a peptide chain can be confirmed using a variety of different techniques well known in the art. For example, expression of a peptide chain can be confirmed using detection reagents, such as antibodies or receptor ligands, specific for an expressed peptide chain. Antibodies that specifically bind to the cyno gp80 peptide chains of the invention are one example of such reagents. gp80 receptor ligands, such as IL-6, dsRNA or poly(I:C) that bind gp80, are additional examples of such reagents. Detection reagents may be detectably labeled by conjugation or incorporation of a radiolabel, fluorophore, chromophore or other detectable molecule to, or into, the detection reagent.

Alternatively, the expression of a cyno gp80 peptide chain of the invention can be confirmed by assaying for a biological activity associated with activation of gp80s, such as an inflammatory response. Such assays may also utilize reporter gene constructs responsive to gp80 activation.

Peptide chain expression can also be confirmed by identification of a peptide chain with the physical characteristics of a peptide chain of the invention in a preparation of peptide chains. For example, SDS-PAGE techniques and other well-known protein characterization techniques utilizing criteria such as, for example, protein molecular weight or isoelectric point can be used to confirm expression of the peptide chains of the invention. Protein purification techniques such as ammonium sulfate or ethanol precipitation, acid extraction, high-performance liquid chromatography, anion or cation exchange chromatography, phosphocellulose chromatography, hydrophobic interaction chromatography, affinity chromatography, hydroxyapatite chromatography and lectin chromatography can also be used to confirm expression of a peptide chain of the invention.

Importantly, in the methods of the invention the peptide chain expressed need not be isolated. Consequently, expression of a peptide chain may be confirmed to have occurred on, or in, a cell, or in a mixture of peptide chains for example. Flow cytometry based techniques such as fluorescence activated cell sorting (FACS) may also be used, when appropriate, to confirm expression of a peptide chain by a cell. As discussed above peptide chain expression may be confirmed using any suitable technique known in the art.

Another embodiment of the invention is a method for expressing a peptide chain comprising the steps of providing a polynucleotide of the invention capable of being transcribed into an RNA coding for at least one peptide chain comprising the sequence set forth in SEQ ID NOS:2, 4, 6, 8, or 10; providing the components of a cell free expression system; initiating cell free expression from the polynucleotide provided; recovering the peptide chain; and, optionally, confirming expression of at least one peptide chain comprising the sequence set forth in SEQ ID NOS:2, 4, 6, 8, or 10.

Techniques for transcribing a polynucleotide into an RNA, obtaining an RNA coding for a peptide chain, or initiating cell free expression are well known in the art and reagent kits for accomplishing these steps are commercially available from a variety of sources.

In another embodiment of the method of the invention the cell free expression system is selected from the group consisting of a reticulocyte lystate based expression system, a wheat germ extract based expression system, and an *Escherichia coli* extract based expression system.

Another embodiment of the invention is a method for expressing a peptide chain comprising the steps of providing an RNA coding for at least one peptide chain comprising the sequence set forth in SEQ ID NOS:2, 4, 6, 8, or 10; providing the components of a cell free expression system; initiating cell free expression from the RNA provided; recovering the peptide chain; and, optionally, confirming expression of at least one peptide chain comprising the sequence set forth in SEQ ID NOS:2, 4, 6, 8, or 10.

In another embodiment of the method of the invention the cell free expression system is selected from the group consisting of a reticulocyte lystate based expression system, a wheat germ extract based expression system, and an *Escherichia coli* extract based expression system.

Another embodiment of the invention is a peptide chain produced by the methods of invention. Such peptide chains may comprise post-translational modifications including glycosylation or phosphorylation for example. Such peptide chains may also comprise alternative peptide chain forms such as splice variants, truncated forms, or proteolytically modified forms.

Another embodiment of the invention is an antibody that specifically binds a peptide chain of the invention. The peptide chains of the invention can be used to produce polyclonal or monoclonal antibodies against cyno gp80. Techniques for making murine, chimeric, humanized and fully human monoclonal antibodies using protein or nucleic acid immunization are routine and well known to those skilled in the art. Additional discussion and description of such techniques can be found above.

Another embodiment of the invention is a monoclonal antibody that specifically binds a peptide chain of the invention.

Another aspect of the invention is a method for determining if a gp80 therapeutic is safe or unsafe comprising providing a gp80 therapeutic, a first cynomolgus monkey, and a second cynomolgus monkey; administering the gp80 therapeutic to the first cynomolgus monkey; and determining whether the first cynomolgus monkey is presenting a deleterious symptom relative to the second monkey, where presentation of a deleterious symptom by the first cynomolgus monkey shows the gp80 therapeutic is unsafe and a lack of presentation of a deleterious symptom by the first cynomolgus monkey shows the gp80 therapeutic is safe.

In the methods of the invention the first and second cynomolgus monkey provided should be equivalent with regard to the presentation of deleterious symptoms. Stated differently both animals should be presenting either no deleterious symptoms or the same deleterious symptoms when they are provided.

In the methods of the invention gp80 therapeutics can be administered by any route appropriate, such as parenterally, subcutaneously, intravenously, etc. Examples of gp80 therapeutics suitable for use in the method of the invention include, for example, known gp80 ligands, such as IL-6 peptides, dsRNA or poly(I:C) and small molecule and biological therapeutics that impact binding of IL-6 to gp80 and resulting signalling.

In the methods of the invention the determination of whether the first cynomolgous monkey is presenting a deleterious symptom relative to the second cynomolgous monkey is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, infections and the like.

In one embodiment of the method of the invention the gp80 therapeutic is an antibody.

The present invention will now be described with reference to the following specific, non-limiting examples.

EXAMPLE 1

Isolation, Cloning and Sequencing of Polynucleotides Encoding Full-Length Cynomolgus gp80

Kidney tissue from a *Macaca fascicularis* (cyno) monkey was obtained from BioChain (Hayward, Calif.). RNA was isolated from kidney tissue from *Macaca fascicularis* (cyno) and reverse transcribed using the Superscript III kit (Invitrogen) into a cDNA pool.

The cynomolgus gp80 gene was then amplified from this cDNA by RT-PCR and sequenced. Using the predicted nucleotide sequence for rhesus gp80 (Genbank Accession XM_001114404), oligos were designed to 5' (nucleotides 383-403 (underlined)) and 3' (nucleotides 1850-1871 (underlined)) untranslated regions (Table 1, SEQ ID NO:9 in which the coding region is from nucleotides 423-1829). It was assumed that a high degree of similarity exists between rhesus and cyno monkeys such that the primers would anneal to the cyno sequence. Using these oligos, RT-PCR was performed using the cyno cDNA pool as a template for amplification. A fragment of approximately 1.5 kb was isolated and subcloned using the TOPO-TA kit (Invitrogen) (FIG. 1). Plasmid DNAs from 8 transformants were isolated and sequenced. The confirmed sequence of cyno gp80 is shown in Table 2.

The sequence of cynomolgus gp80 protein is 97% identical to the human gp80 amino acid sequence. A sequence comparison of the human and cyno gp80 nucleotide sequences is shown in Table 3, and amino acid sequences in Table 4. This high degree of conservation suggests that the cynomolgus monkey is a relevant toxicology study animal for the in vivo evaluation of compounds that target gp80 (or alternatively IL-6).

RT-PCR was performed using oligos based on the rhesus 5' and 3' UTR on a cDNA pool derived from cyno kidney tissue as a template for amplification. PCR products were separated by agarose gel electrophoresis and visualized under UV light. This is shown in FIG. 1. A fragment of approximately 1.5 kb was expected; the band indicated by the red arrow was isolated (NTC=No Template Control; MW=Molecular Weight marker).

It will be clear to one of ordinary skill in the art that the invention now being fully described can be practiced otherwise than as particularly described in the foregoing description and examples. Numerous modifications and variations of the present invention are possible in light of the above teachings and, therefore, are within the scope of the appended claims and equivalents.

TABLE 1

Nucleotide Sequence of rhesus gp80

(SEQ ID NO: 9)

```
   1 GGCGGTCCCCTGTTC TCCCCGCTCAGGTGC GGCGCTGTGGCAGGA AGCCACCCCCTCGGT CGGCCGGTGCGCGGG
  76 GCTGTTGCGCCATCC GCTCCAGCTTTCGTA ACCGCACCCTGGGAC GGCCCAGAGACGCTC CAGCGCGAGTTCCTC
 151 AAATGTTTTCCTGTG TTGCCAGGACCGTCC GCCGCTCTGAGTCAT GTGCGAGTGGGAAGT CTCACTGACACTGAG
 226 ACCGGCCAGTGGGAG CGGAGCCGAGCGCGG CGCGGGGCTGAGGGA CTCGCAGTGTATATA GAGCGCCGGGCTCCT
 301 GCGATGGGGGCTGCC CCCGGAGACTGAGCC AGCCTGCCCGCCCAC CGCCCCGCCCCTGCC GCCCGGTTCCCACCA
 376 GCCTGTCCGCCTCTG CGGGACCATGGAGCG GTAGCCGAGGAGGAA GCATGCTGGCCGTCG GCTGCGCGCTGCTGG
 451 CTGCCCTGCTGGCCG CGCCGGGGCGGCGC TGGCCCCGGGGGGCT GCCCTGCGCAGGAGG TGGCGAGAGGTGTGC
 526 TGACCAGTCTGCCAG GAGACAGCGTGACTC TGACCTGCCCAGGGG GAGAGCCGGAAGACA ATGCCACTGTTCACT
 601 GGGTTCTCAGGAAGC CAGCTGTAGGCTCCC ACCTCAGCAGATGGG CTGGCGTGGGAAGGA GGCTGCTGCTGAGGT
 676 CGGTGCAGCTCCATG ACTCTGGAAACTATT CATGCTACCGGGCCG GCCGCCCGGCTGGAA CTGTGCACTTGCTGG
 751 TGGATGTTCCCCCCG AGGAGCCCCAGCTCT CCTGCTTCCGGAAGA GCCCCCTCAGCAACG TTGTTTGTGAGTGGG
 826 GTCCTCGGAGCACCC CATCTCCGACGACCA AGGCTGTGCTGTTGG TGAGGAAGTTTCAGA ACAGTCCGGCCGAAG
 901 ACTTCCAGGAGCCGT GCCAGTATTCCCAGG AGTCCCAGAAGTTCT CCTGCCAGTTGGCAG TCCCGGAGGGAGACA
 976 GCTCTTTCTACATAG TGTCCATGTGCGTCG CCAGTAGTGTCGGGA GCAAGCTCAGCAAAA CTCAGACCTTTCAGG
1051 GTTGTGGAATCTTGC AGCCTGATCCGCCTG CCAACATCACAGTCA CTGCCGTGGCCAGAA ACCCCGCTGGCTCA
1126 GTGTCACCTGGCAAG ACCCCCACTCCTGGA ACTCATCTTTCTACA GACTACGGTTTGAGC TCAGATATCGAGCTG
1201 AACGGTCAAAGACAT TCACAACATGGATGG TCAAGGACCTCCAGC ATCACTGTGTCATCC ACGACGCCTGGAGCG
1276 GCCTGAGGCACGTGG TGCAGCTTCGTGCCC AGGAGGAGTTCGGGC AAGGCGAGTGGAGCA AGTGGAGCCCGGAGG
1351 CCATGGGCACGCCTT GGACAGAATCCAGGA GTCCTCCAGCTGAGA ACGAGGTGTCCACCC CACGCAGGCACCTA
1426 CTACTAATAAAGATG ATGATAATATTCTCT CCAGAGATTCTGCAA ATGCGACAAGCCTCC CAGTGCAAGATTCTT
1501 CTTCGGTACCACTGC CCACATTCCTGGTTG CTGGAGGGAGCCTGG CGTTCGGAACGCTCC TGTGCATTGCCATTG
1576 TTCTGAGGTTCAAGA AGACGTGGAAGCTGC GGGCTCTGAAGGAAG GCAAGACAAGCATGC ACCCGCCGTATTCTT
1651 TGGGGCAGCTGGTCC CAGAGAGGCCGCGAC CCACCCCAGTGCTTG TTCCTCTCATCTCCC CACCAGTGTCCCCA
1726 GCAGCCTGGGGTCTG ACAACACCTCGAGCC ACAACCGACCAGATG CCAGGGACCCACGGA GCCCTTACGACATCA
1801 GCAATACAGACTACT TCTTCCCCAGATAGT TGGCCAGGGGCACT AGCAGGCTGGACCCT GTGGATGACAGAGCA
1876 CAAACGGGCTCAGCA AAGGATGCTTCTTAC TGCCATGCCAGCTTA TCTCAGGGGAGTGGG GCCTTTGGCTTCACG
1951 GAAGAGCCTTGCGGA AGGTTCGACACCAGG GGAAAATCAGCCTGC TCCAGCTGTTCAGCT GGTTGAGATTTCAAA
2026 CCTCCCTTTCCAAAT GTCTGGCTTAAAGGG GTTAGAGTGAACTTG GCCACTGTGAAGAG AAGCATGTCAAGACT
2101 CTTTGGACATTCAAC ACGGACACTCAAAAG CTGGGCAGCTTGGTG GGGGCCTCAGTGTGG AGAAGCGGCTGGCAG
2176 CCCACCCCCAACAC CTCTGCACAAGCTGC GCCCTCAGGCAGGGG GGCGGATTTCCAGC CAAAGCCTCCTTCAG
2251 CCGCCACGCTCCTGG CCCACTGCATCATTT CATCTTCCAGCTCAA ACTCCTAAAACCCAA GTGCCTTTGCAAATT
2326 CTGTTTTTCTGAGCC TGGGGACGGCTTTTA CTTAAACCGCCAAGG CTGGGGAAAGAAGCT CTCTCCTCCCTTTCT
2401 TCCCCACAGTTGAAA AACAGCTGAGGGTGG GTGGGTGAATAATAC AGTATCTCAGGGCCT GGTCGTTTTCAACGG
2476 AATTATAATTAGTTC CTCATTAGCATTTTG CTAAATGTGAATGAT AATCCTAGGCATTTG CTGAATACAGAGGCA
2551 ACTGCATTGGCTTTG GGTTGCAGGACCTCA GGTGAGAAGCAGAGG AAGGAGAGGAGAGGG GCACAGGGTCTCCAC
2626 CATCCCCTGTAGAGT GGGAGCTGCGCGGGG GATCACAGCCTCTGA AAACCAATGTTCTCT GTTCTCCACCTCCCA
2701 CAAAGGAGAGCTGGC AGCAGGGAGGGCTTC TGCCAGTGCTGAGAT CAAAACTGTTTTACT GCAGCTTTGTTTGTT
```

TABLE 1-continued

Nucleotide Sequence of rhesus gp80

```
2776 GTCAGCCGAACCTGG GTAACTAGGGAAGAT AATATTAAGGAAGAC AATGTGAAAAGAAAA ATGAGCCCGGCAAGA
2851 ATGCATTTTAACTTG GTTTTTAAAAAACTG CTGACTGTTTTCTCT TGAGAGGGTGGAATA TCCAATATGCGCTGT
2926 GTCAGCATAGAAGTA ACTTACTTAGGTGTG GGGGAAGCACCATAA CTTTGTTTAGCCCAA AACTAAGTCAAGTGA
3001 AAAAGGAGGAAGAGA AATAATATTTTTCCT GCCAGGCATGGTGGT TCACGCCTGTAATCC CAGCACTCTGGGAGG
3076 TCGAGGCGGGACGAT CACTTGAGTCCAGGA GTTTGAGACCAGCCT GGGCAATGTGGTAAA ACCTCATCTCGACAA
3151 AAAGCATAAAAATTA GCCAGGTATGGTAGA GTGCACCTGAAGTCC CAGTTAGTTGGGAGG CTGAGGTGGGAGGAT
3226 CTCTTGAGCCTGGGA GGTCAAGGCTGCAGT GAGCCGAGATTGCAC CACTGCACTCCAGCC TGGGTGACTGAGCAA
3301 GTGAGACCCTGTCTC AAAAAAGAAAAGGAA AAAGAAAAGAAAAAA TATTTTCCCTGTTAG AGAAGAGATTGTGGT
3376 TTCATTGTGTATTTT GTTTTTGTCTTAAAA AGTGGAAAAATAGCC TGCCTCTTCTCTACT CTAGGGAAAAACCAG
3451 TGTGTGACTACTCCC CCAGGCGGTTATGGA GAGGGCGTCCGGTCC CTGTCCCAGTGCTGA GAAGGGAGCCTCCCA
3526 CGACTACCCGGCAGG GTCCTAGAAATTCCC CACCCTGAAAGCCCT GAGCCTTCTGCTATC AAAGGGGCAGGTAAA
3601 AATCCCATTTAAAAA AAATCCCTTACCTCG GTGCCTTCCTCTTTT TATTTAGCTCCTTGA GTTGATTCAGCTCTG
3676 CAAGAATTGAAGCAG AACTAAATGTCTAAT TGTAACACCGTGATT AACCACTTCAGCTGA CTTTTCTGCCCGAGC
3751 TTTGAAAATTCAGTG GTGTTAGTGGTTACC CAGTTAGCTCTCAAG TTATCAGGGTACTCC ACAGCGGGGATATAC
3826 CAGACCACAAAACCT TTCTAATACTCTACC CTCTTAGAAAAACAG CCACCATCACCAGAC AGGTGCAAAAGGAGG
3901 AAAGTGACCATGTTT TGTTTACCGTTTTCC AGGTTTAAGCTGTTA CTGTCTTCAGCAAGC CGTGCTTTTCATTGC
3976 TGGGTTTGTCTGTAG ATTTTAGACCCTATT GCTGCTTGAGGCACC TCATCTTAAGTTGGC AAAAAGGCAGGACGG
4051 CTGGGTGTGGTGGCT CACGCCTGTAATCCT AGCACTTTGGGAGGC CGAGGTGGGAGGATT GCTTGAGCTCAGGAA
4126 TTTGAGACCAACCTG GGTAACATAGTGAGA TACCATCTCTATTAT AAACAATAACATTTA AGGAAAAAAAAGGC
4201 AGGCAGGTGGTTATG GTGGTTCCCTCCCAT CCTGCTGCATAAAGT TTCTGAGACTTGAGA ACAGCAAAAATGCTG
4276 TTAAAGGGAAATATT AAGAATGAGAATCTG CATGAAGGGTGATTA TGTGCCCACAGTTAA TTCTTTATACCGTTT
4351 TACCCACATGTGGTA TTACCGAAGCCGGGC AGAACCATGCTAGCG GAAGATATGAAATTC AGATAGCTCATTATT
4426 GCCAAGAGCTAGGCA GCTTTGATCTCCAAA TTGTTATTGCTTTCA TTTTTATTGTAATGG AACTGCTTTTTTTTT
4501 TTTTTTTTTTTTTTT TGCTTTTTTTTCTTT GTTTTGTTTTGTAG TGAAGAGGGTTTTTT TCCCTTTATTTTCA
4576 TAAGCTACTGTAAAT GAAGAAAAGTGTCT TCTCTGGGCTGTAGG CCTGGCTCAGTGTAC ACAGGTATACATCCT
4651 AAGCTCTCTCTGTTC TCTAATTTGTGGTGA CTGAATATGTGTCGC AATCCACGGGCATT TCTACCTGTATTTCT
4726 GCAGCACCCCCACTG CCTTGAGTCCCCAGC AGTGCTGTTATTTGC CTAATACCTGTAGCC ATCTGCCACACAGCC
4801 AGACATGAAACGCTG GGACAGAGACCATTT AGATTAAATACAACA GCTTATCTTGCTGGG TGGGGAAAGTAAAAA
4876 ATATGCTGGTTCAAG GTCTAAAGTAAAATG ATAAATAATGTTTGT AGCATTAATGAAATA TTTTCAAGAAATGTG
4951 TCCGGGGGTAGCATT GGCTATGCTGACGAG GCCTTTGGTAACTCA GAAAGCTCTTGGCCC CGATGGCGACTTGCC
5026 CTTGCACTTTCTTTA TCAGGCTCTGAGCTC ACACGGAGCCTCTGG CATTTCCCTGCTGTC TTGGGAGAAAGGAAA
5101 CTGGTTGTGGCGGCA GGGTGTGGAATCTGC TGCTGGAACCAGGCT GGAAGCCCACCTGGT AGTGAACAGGGCCCA
5176 GCGGGGCAGGCTAGG AGTGTTGTGGTCTAT GGGTTTGTGTCCTGG AGAATGTTCAAGAAT GTCTTCTTGGCTGCT
5251 TTGGTGCTGAGCTCT GTTATCTCACAGCAC GTCCTGAAGGCTAAC CCAGGTGGGAGGAT GCTGACACCAGCTCC
5326 AGGTGGAGTTGGTGA GAAATCTGTCTTAAC TTGGAGATGCAGGGG CAACCTGTGACCCTT TGAGGCAAGAGCCCT
5401 GCACCCAGCTGTCCC GTGCAGCCGTGGGCA GGGGGCTGCACATGG AGGGGCAGGCGGGCC AGTTCAGGGCCAGTT
5476 CAGTGCCCTGTAAGG GCCCTTCAGCCTCCT GTCCTCTGTGCGGCT GGGCGCCAGCACCAG GGAGTTTCTATGGCA
5551 ACCTTAGTGATTATT AAGGAACATTGTCAG TTTTATGAACATATG CTCAAATGAAATTCT ACTTTAGGAGGAAAG
5626 GATTGGAACAGCATG TTGCAAGGCTGTTAA TTAACAGAGAGACCT TATTGGATGGAGATC ACATCTGTTAAATAG
```

TABLE 1-continued

Nucleotide Sequence of rhesus gp80

```
5701 AATACCTCAACTCTA CGTTGTTTTCTTGGA GATAAATAATAGTTT CAAGTTTTTGTTTGT TGTTTTACCTAATT

5776 ACCTGAAAGCAAATA CCAAAGGCTGATGTC TGTATATGGGCAAA GGGTCAGTATATTTT TCAGTGTTTTTTTT

5851 CTTTTACAAGCTATT TTGCATTTAAAGTGA ACATTGTAAATGTTT GTAATAAATGATTTT TAAAAATACA
```

TABLE 2 cDNA and amino acid sequence of cyno gp80. The encoded protein sequence (SEQ ID NO: 2) is shown above the nucleotide sequence (SEQ ID NO: 1).

```
           M   L   A   V   G   C   A   L   L   A   A   L   L   A   T
    1      ATGCTGGCC GTCGGCTGC GCGCTGCTG GCTGCCTTG CTGGCCACG

P   G   A   A   L   A   P   G   G   C   P   A   Q   E   V
   46      CCGGGGGCG GCGCTGGCC CCGGGGGGC TGCCCTGCA CAGGAGGTG

A   R   G   V   L   T   S   L   P   G   D   S   V   T   L
   91      GCGAGAGGT GTGCTGACC AGTCTGCCA GGAGACAGC GTGACTCTG

T   C   P   G   G   E   P   E   D   N   A   T   V   H   W
  136      ACCTGCCCA GGGGGAGAG CCGGAAGAC AATGCCACT GTTCACTGG

V   L   R   K   P   A   E   G   S   H   L   S   R   W   A
  181      GTTCTCAGG AAGCCAGCT GAAGGCTCC CACCTCAGC AGATGGGCT

G   V   G   R   R   L   L   R   S   V   Q   L   H   D
  226      GGCGTGGGA AGGAGGCTG CTGCTGAGG TCGGTGCAG CTCCATGAC

S   G   N   Y   C   Y   R   A   G   R   P   A   A   T
  271      TCTGGAAAC TATTCATGC TACCGGGCC GGCCGCCCG GCTGCAACT

V   H   L   V   D   V   P   P   E   E   P   Q   L   S
  316      GTGCACTTG CTGGTGGAT GTTCCCCCC GAGGAGCCC CAGCTCTCC

C   F   R   K   S   P   L   S   N   V   V   C   E   W   G
  361      TGCTTCCGG AAGAGCCCA CTCAGCAAC GTTGTTTGT GAGTGGGGT

P   R   S   T   P   S   P   T   T   K   A   V   L   L   V
  406      CCTCGGAGC ACCCCATCT CCGACGACC AAGGCTGTG CTGTTGGTG

R   K   F   Q   N   S   P   A   E   D   F   Q   E   P   C
  451      AGGAAGTTT CAGAACAGT CCGGCCGAA GACTTCCAG GAGCCGTGC

Q   Y   S   Q   E   S   Q   K   F   S   C   Q   L   A   V
  496      CAGTATTCC CAGGAGTCC CAGAAGTTC TCCTGCCAG TTGGCAGTC

P   E   G   D   S   S   F   Y   I   V   S   M   C   V   A
  541      CCGGAGGGA GACAGCTCT TTCTACATA GTGTCCATG TGCGTCGCC

S   S   V   G   S   K   L   S   K   T   Q   T   F   Q   G
  586      AGTAGTGTC GGGAGCAAG CTCAGCAAA ACTCAGACC TTTCAGGGT

C   G   I   L   Q   P   D   P   P   A   N   I   T   V   T
  631      TGTGGAATC TTGCAGCCT GATCCGCCT GCCAACATC ACAGTCACT

A   V   A   R   N   P   R   W   L   S   V   T   W   Q   D
  676      GCCGTGGCC AGAAACCCC CGCTGGCTC AGTGTCACC TGGCAAGAC

P   H   S   W   N   S   S   F   Y   R   L   R   F   E   L
  721      CCCCACTCC TGGAACTCA TCTTTCTAC AGACTACGG TTTGAGCTC

R   Y   R   A   E   R   S   K   T   F   T   T   W   M   V
  766      AGATATCGA GCTGAACGG TCAAAGACA TTCACAACA TGGATGGTC

K   D   L   Q   H   H   C   V   I   H   D   A   W   S   G
  811      AAGGACCTC CAGCATCAC TGTGTCATC CACGACGCC TGGAGCGGC

L   R   H   V   V   Q   L   R   A   Q   E   E   F   G   Q
  856      CTGAGGCAC GTGGTGCAG CTTCGTGCC CAGGAGGAG TTCGGGCAA

G   E   W   S   E   W   S   P   E   A   M   G   T   P   W
  901      GGCGAGTGG AGCGAGTGG AGCCCGGAG GCCATGGGC ACGCCTTGG
```

TABLE 2-continued cDNA and amino acid sequence of cyno gp80. The encoded
protein sequence (SEQ ID NO: 2) is shown above the
nucleotide sequence (SEQ ID NO: 1).

```
            T   E   S       R   S   P       P   A   E       N   E   V       S   T   P
 946        ACAGAATCC   AGGAGTCCT   CCAGCTGAG   AACGAGGTG   TCCACCCCC

T   Q   A       P   T   T       N   K   D       D   D   N       I   L   S
 991        ACGCAGGCA   CCTACTACT   AATAAAGAT   GATGATAAT   ATTCTCTCC

G   D   S       A   A   A       T   S   L       P   V   Q       D   S   S
1036        GGAGATTCT   GCAAATGCG   ACAAGCCTC   CCAGTGCAA   GATTCTTCT

S   V   P       L   P   T       F   L   V       A   G   G       S   L   A
1081        TCGGTACCA   CTGCCCACA   TTCCTGGTT   GCTGGAGGG   AGCCTGGCG

F   G   T       L   L   C       I   A   I       V   L   R       F   K   K
1126        TTCGGAACG   CTCCTGTGC   ATTGCCATT   GTTCTGAGG   TTCAAGAAG

T   W   K       L   R   A       L   K   E       G   K   T       S   M   H
1171        ACGTGGAAG   CTGCGGGCT   CTGAAGGAA   GGCAAGACA   AGCATGCAC

P   P   Y       S   L   G       Q   L   V       P   E   R       P   R   P
1216        CCGCCGTAT   TCTTTGGGG   CAGCTGGTC   CCAGAGAGG   CCGCGACCC

T   P   V       L   V   P       L   I   S       P   P   V       S   P   S
1261        ACCCCAGTG   CTTGTTCCT   CTCATCTCC   CCACCAGTG   TCCCCCAGT

S   L   G       S   D   N       T   S   S       H   N   R       P   D   A
1306        AGCCTGGGG   TCTGACAAC   ACCTCGAGC   CACAACCGA   CCAGATGCC

R   D   P       R   S   P       Y   D   I       S   N   T       D   Y   F
1351        AGGGACCCA   CGGAGCCCT   TACGACATC   AGCAATACA   GACTACTTC

F   P   R       *
1396        TTCCCCAGA   TAG
```

TABLE 3

Alignment of human vs. cyno gp80. The nucleotide sequences for human
(Genbank Accession BC132684) (SEQ ID NO: 12) and cyno gp80
(SEQ ID NO: 1) are aligned and are 97% identical
(divergent residues shown in bold). The consensus sequence
(SEQ ID NO: 13) is shown under the aligned human and cyno
gp80 sequences.

```
cyno   gp80    (1) ATGCTGGCCGTCGGCTGCGCGCTGCTGGCTGCCTTGCTGGCCACGCCGGG
human  gp80    (1) ATGCTGGCCGTCGGCTGCGCGCTGCTGGCTGCCCTGCTGGCCGCGCCGGG cyno   gp80   (51) GGCGGCGCTGGCCCCGGGGGGCTGCCCTGCACAGGAGGTGGCGAGAGGTG
human  gp80   (51) AGCGGCGCTGGCCCCAAGGCGCTGCCCTGCGCAGGAGGTGGCGAGAGGCG cyno   gp80  (101) TGCTGACCAGTCTGCCAGGAGACAGCGTGACTCTGACCTGCCCAGGGGGA
human  gp80  (101) TGCTGACCAGTCTGCCAGGAGACAGCGTGACTCTGACCTGCCCGGGGGTA cyno   gp80  (151) GAGCCGGAAGACAATGCCACTGTTCACTGGTTCTCAGGAAGCCAGCTGA
human  gp80  (151) GAGCCGGAAGACAATGCCACTGTTCACTGGTGCTCAGGAAGCCGGCTGC cyno   gp80  (201) AGGCTCCCACCTCAGCAGATGGGCTGGCGTGGAAGGAGGCTGCTGCTGA
human  gp80  (201) AGGCTCCCACCCCAGCAGATGGGCTGGCATGGAAGGAGGCTGCTGCTGA cyno   gp80  (251) GGTCGGTGCAGCTCCATGACTCTGGAAACTATTCATGCTACCGGGCCGGC
human  gp80  (251) GGTCGGTGCAGCTCCACGACTCTGGAAACTATTCATGCTACCGGGCCGGC cyno   gp80  (301) CGCCCGGCTGCAACTGTGCACTTGCTGGTGGATGTTCCCCCCGAGGAGCC
human  gp80  (301) CGCCCAGCTGGGACTGTGCACTTGCTGGTGGATGTTCCCCCCGAGGAGCC cyno   gp80  (351) CCAGCTCTCCTGCTTCCGGAAGAGCCCACTCAGCAACGTTGTTTGTGAGT
human  gp80  (351) CCAGCTCTCCTGCTTCCGGAAGAGCCCCCTCAGCAATGTTGTTTGTGAGT cyno   gp80  (401) GGGGTCCTCGGAGCACCCCATCTCCGACGACCAAGGCTGTGCTGTTGGTG
human  gp80  (401) GGGGTCCTCGGAGCACCCCATCCCTGACGACAAAGGCTGTGCTCTTGGTG cyno   gp80  (451) AGGAAGTTTCAGAACAGTCCGGCCGAAGACTTCCAGGAGCCGTGCCAGTA
human  gp80  (451) AGGAAGTTTCAGAACAGTCCGGCCGAAGACTTCCAGGAGCCGTGCCAGTA
```

TABLE 3-continued

Alignment of human vs. cyno gp80. The nucleotide sequences for human (Genbank Accession BC132684) (SEQ ID NO: 12) and cyno gp80 (SEQ ID NO: 1) are aligned and are 97% identical (divergent residues shown in bold). The consensus sequence (SEQ ID NO: 13) is shown under the aligned human and cyno gp80 sequences.

```
cyno   gp80  (501)  TTCCCAGGAGTCCCAGAAGTTCTCCTGCCAGTTGGCAGTCCCGGAGGGAG
human  gp80  (501)  TTCCCAGGAGTCCCAGAAGTTCTCCTGCCAGTTAGCAGTCCCGGAGGGAG cyno   gp80  (551)  ACAGCTCTTTCTACATAGTGTCCATGTGCGTCGCCAGTAGTGTCGGGAGC
human  gp80  (551)  ACAGCTCTTTCTACATAGTGTCCATGTGCGTCGCCAGTAGTGTCGGGAGC cyno   gp80  (601)  AAGCTCAGCAAAACTCAGACCTTTCAGGGTTGTGGAATCTTGCAGCCTGA
human  gp80  (601)  AAGTTCAGCAAAACTCAAACCTTTCAGGGTTGTGGAATCTTGCAGCCTGA cyno   gp80  (651)  TCCGCCTGCCAACATCACAGTCACTGCCGTGGCCAGAAACCCCCGCTGGC
human  gp80  (651)  TCCGCCTGCCAACATCACAGTCACTGCCGTGGCCAGAAACCCCCGCTGGC cyno   gp80  (701)  TCAGTGTCACCTGGCAAGACCCCCACTCCTGGAACTCATCTTTCTACAGA
human  gp80  (701)  TCAGTGTCACCTGGCAAGACCCCCACTCCTGGAACTCATCTTTCTACAGA cyno   gp80  (751)  CTACGGTTTGAGCTCAGATATCGAGCTGAACGGTCAAAGACATTCACAAC
human  gp80  (751)  CTACGGTTTGAGCTCAGATATCGGGCTGAACGGTCAAAGACATTCACAAC cyno   gp80  (801)  ATGGATGGTCAAGGACCTCCAGCATCACTGTGTCATCCACGACGCCTGGA
human  gp80  (801)  ATGGATGGTCAAGGACCTCCAGCATCACTGTGTCATCCACGACGCCTGGA cyno   gp80  (851)  GCGGCCTGAGGCACGTGGTGCAGCTTCGTGCCCAGGAGGAGTTCGGGCAA
human  gp80  (851)  GCGGCCTGAGGCACGTGGTGCAGCTTCGTGCCCAGGAGGAGTTCGGGCAA cyno   gp80  (901)  GGCGAGTGGAGCGAGTGGAGCCCGGAGGCCATGGGCACGCCTTGGACAGA
human  gp80  (901)  GGCGAGTGGAGCGAGTGGAGCCCGGAGGCCATGGGCACGCCTTGGACAGA cyno   gp80  (951)  ATCCAGGAGTCCTCCAGCTGAGAACGAGGTGTCCACCCCCACGCAGGCAC
human  gp80  (951)  ATCCAGGAGTCCTCCAGCTGAGAACGAGGTGTCCACCCCCATGCAGGCAC cyno   gp80 (1001)  CTACTACTAATAAAGATGATGATAATATTCTCTCCGGAGATTCTGCAAAT
human  gp80 (1001)  TTACTACTAATAAAGACGATGATAATATTCTCTTCAGAGATTCTGCAAAT cyno   gp80 (1051)  GCGACAAGCCTCCCAGTGCAAGATTCTTCTTCGGTACCACTGCCCACATT
human  gp80 (1051)  GCGACAAGCCTCCCAGTGCAAGATTCTTCTTCAGTACCACTGCCCACATT cyno   gp80 (1101)  CCTGGTTGCTGGAGGGAGCCTGGCGTTCGGAACGCTCCTGTGCATTGCCA
human  gp80 (1101)  CCTGGTTGCTGGAGGGAGCCTGGCCTTCGGAACGCTCCTCTGCATTGCCA cyno   gp80 (1151)  TTGTTCTGAGGTTCAAGAAGACGTGGAAGCTGCGGGCTCTGAAGGAAGGC
human  gp80 (1151)  TTGTTCTGAGGTTCAAGAAGACGTGGAAGCTGCGGGCTCTGAAGGAAGGC cyno   gp80 (1201)  AAGACAAGCATGCACCCGCCGTATTCTTTGGGGCAGCTGGTCCCAGAGAG
human  gp80 (1201)  AAGACAAGCATGCATCCGCCGTACTCTTTGGGGCAGCTGGTCCCGGAGAG cyno   gp80 (1251)  GCCGCGACCCACCCCAGTGCTTGTTCCTCTCATCTCCCCACCAGTGTCCC
human  gp80 (1251)  GCCTCGACCCACCCCAGTGCTTGTTCCTCTCATCTCCCCACCGGTGTCCC cyno   gp80 (1301)  CCAGTAGCCTGGGGTCTGACAACACCTCGAGCCACAACCGACCAGATGCC
human  gp80 (1301)  CCAGCAGCCTGGGGTCTGACAATACCTCGAGCCACAACCGACCAGATGCC cyno   gp80 (1351)  AGGGACCCACGGAGCCCTTACGACATCAGCAATACAGACTACTTCTTCCC
human  gp80 (1351)  AGGGACCCACGGAGCCCTTATGACATCAGCAATACAGACTACTTCTTCCC cyno   gp80 (1401)  CAGATAG
human  gp80 (1401)  CAGATAG
```

TABLE 4

Alignment of human and cyno gp80.
The predicted amino acid sequences for human (SEQ ID NO: 11) and cyno gp80 (SEQ ID NO: 2) are aligned. The cyno sequence is 97% identical to the human sequence, respectively (divergent residues shown in bold).

```
                              1                                                50
cyno gp80            (1)  MLAVGCALLAALLATPGAALAPGGCPAQEVARGVLTSLPGDSVTLTCPGG
human gp80 v1 NM_000565 (1)  MLAVGCALLAALLAAPGAALAPRRCPAQEVARGVLTSLPGDSVTLTCPGV
           Consensus  (1)  MLAVGCALLAALLA PGAALAP  CPAQEVARGVLTSLPGDSVTLTCPG
                              51                                              100
```

TABLE 4-continued

Alignment of human and cyno gp80.
The predicted amino acid sequences for human (SEQ ID NO: 11) and cyno gp80
(SEQ ID NO: 2) are aligned. The cyno sequence is 97% identical to the human
sequence, respectively (divergent residues shown in bold).

```
      cyno gp80             (51)  EPEDNATVHWVLRKPAEGSHLSRWAGVGRRLLLRSVQLHDSGNYSCYRAG
human gp80 v1 NM_000565     (51)  EPEDNATVHWVLRKPAAGSHPSRWAGMGRRLLLRSVQLHDSGNYSCYRAG
                  Consensus (51)  EPEDNATVHWVLRKPA GSH SRWAGMGRRLLLRSVQLHDSGNYSCYRAG
                                  101                                              150
      cyno gp80            (101)  RPAATVHLLVDVPPEEPQLSCFRKSPLSNVVCEWGPRSTPSPTTKAVLLV
human gp80 v1 NM_000565    (101)  RPAGTVHLLVDVPPEEPQLSCFRKSPLSNVVCEWGPRSTPSLTTKAVLLV
                  Consensus (101) RPAATVHLLVDVPPEEPQLSCFRKSPLSNVVCEWGPRSTPS TTKAVLLV
                                  151                                              200
      cyno gp80            (151)  RKFQNSPAEDFQEPCQYSQESQKFSCQLAVPEGDSSFYIVSMCVASSVGS
human gp80 v1 NM_000565    (151)  RKFQNSPAEDFQEPCQYSQESQKFSCQLAVPEGDSSFYIVSMCVASSVGS
                  Consensus (151) RKFQNSPAEDFQEPCQYSQESQKFSCQLAVPEGDSSFYIVSMCVASSVGS
                                  201                                              250
      cyno gp80            (201)  KLSKTQTFQGCGILQPDPPANITVTAVARNPRWLSVTWQDPHSWNSSFYR
human gp80 v1 NM_000565    (201)  KFSKTQTFQGCGILQPDPPANITVTAVARNPRWLSVTWQDPHSWNSSFYR
                  Consensus (201) K SKTQTFQGCGILQPDPPANITVTAVARNPRWLSVTWQDPHSWNSSFYR
                                  251                                              300
      cyno gp80            (251)  LRFELRYRAERSKTFTTWMVKDLQHHCVIHDAWSGLRHVVQLRAQEEFGQ
human gp80 v1 NM_000565    (251)  LRFELRYRAERSKTFTTWMVKDLQHHCVIHDAWSGLRHVVQLRAQEEFGQ
                  Consensys (251) LRFELRYRAERSKTFTTWMVKDLQHHCVIHDAWSGLRHVVQLRAQEEFGQ
                                  301                                              350
      cyno gp80            (301)  GEWSEWSPEAMGTPWTESRSPPAENEVSTPTQAPTTNKDDDNILSGDSAN
human gp80 v1 NM_000565    (301)  GEWSEWSPEAMGTPWTESRSPPAENEVSTPMQALTTNKDDDNILFRDSAN
                  Consensus (301) GEWSEWSPEAMGTPWTESRSPPAENEVSTP QA TTNKDDDNIL  DSAN
                                  351                                              400
      cyno gp80            (351)  ATSLPVQDSSSVPLPTFLVAGGSLAFGTLLCIAIVLRFKKTWKLRALKEG
human gp80 v1 NM_000565    (351)  ATSLPVQDSSSVPLPTFLVAGGSLAFGTLLCIAIVLRFKKTWKLRALKEG
                  Consensus (351) ATSLPVQDSSSVPLPTFLVAGGSLAFGTLLCIAIVLRFKKTWKLRALKEG
                                  401                                              450
      cyno gp80            (401)  KTSMHPPYSLGQLVPERPRPTPVLVPLISPPVSPSSLGSDNTSSHNRPDA
human gp80 v1 NM_000565    (401)  KTSMHPPYSLGQLVPERPRPTPVLVPLISPPVSPSSLGSDNTSSHNRPDA
                  Consensus (401) KTSMHPPYSLGQLVPERPRPTPVLVPLISPPVSPSSLGSDNTSSHNRPDA
                                  451           469
      cyno gp80            (451)  RDPRSPYDISNTDYFFPR-
human gp80 v1 NM_000565    (451)  RDPRSPYDISNTDYFFPR-
                  Consensus (451) RDPRSPYDISNTDYFFPR
```

SEQ ID NO: 1
(signal sequence single underlined) (transmembrane domain double underlined)
<u>ATGCTGGCCGTCGGCTGCGCGCTGCTGGCTGCCTTGCTGGCCACGCCGGGGGCGGCGCTG</u>CCCCGGGGGCTGCCCTGCAC
AGGAGGTGGCGAGAGGTGTGCTGACCAGTCTGCCAGGAGACAGCGTGACTCTGACCTGCCCAGGGGAGAGCCGGAAGACAA
TGCCACTGTTCACTGGGTTCTCAGGAAGCCAGCTGAAGGCTCCCACCTCAGCAGATGGGCTGGCGTGGGAAGGAGGCTGCTG
CTGAGGTCGGTGCAGCTCCATGACTCTGGAAACTATTCATGCTACCGGGCCGGCCGCCCGGCTGCAACTGTGCACTTGCTGG
TGGATGTTCCCCCCGAGGAGCCCCAGCTCTCCTGCTTCCGGAAGAGCCCACTCAGCAACGTTGTTTGTGAGTGGGGTCCTCG
GAGCACCCCATCTCCGACGACCAAGGCTGTGCTGTTGGTGAGGAAGTTTCAGAACAGTCCGGCCGAAGACTTCCAGGAGCCG
TGCCAGTATTCCCAGGAGTCCCAGAAGTTCTCCTGCCAGTTGGCAGTCCCGGAGGGAGACAGCTCTTTCTACATAGTGTCCA
TGTGCGTCGCCAGTAGTGTCGGGAGCAAGCTCAGCAAAACTCAGACCTTTCAGGGTTGTGGAATCTTGCAGCCTGATCCGCC
TGCCAACATCACAGTCACTGCCGTGGCCAGAAACCCCCGCTGGCTCAGTGTCACCTGGCAAGACCCCCACTCCTGGAACTCA
TCTTTCTACAGACTACGGTTTGAGCTCAGATATCGAGCTGAACGGTCAAAGACATTCACAACATGGATGGTCAAGGACCTCC
AGCATCACTGTGTCATCCACGACGCCTGGAGCGGCCTGAGGCACGTGGTGCAGCTTCGTGCCCAGGAGGAGTTCGGGCAAGG
CGAGTGGAGCGAGTGGAGCCCGGAGGCCATGGGCACGCCTTGGACAGAATCCAGGAGTCCTCCAGCTGAGAACGAGGTGTCC
ACCCCCACGCAGGCACCTACTACTAATAAAGATGATGATAATATTCTCTCCGGAGATTCTGCAAATGCGACAAGCCTCCCAG
TGCAAGATTCTTCTTCGGTA<u>CCACTGCCCACATTCCTGGTTGCTGGAGGGAGCCTGGCGTTCGGAACGCTCCTGTGCATTGC
CATTGTTCTG</u>AGGTTCAAGAAGACGTGGAAGCTGCGGGCTCTGAAGGAAGGCAAGACAAGCATGCACCCGCCGTATTCTTTG
GGGCAGCTGGTCCCAGAGAGGCCGCGACCCACCCCAGTGCTTGTTCCTCTCATCTCCCCACCAGTGTCCCCCAGTAGCCTGG
GGTCTGACAACACCTCGAGCCACAACCGACCAGATGCCAGGGACCCACGGAGCCCTTACGACATCAGCAATACAGACTACTT
CTTCCCCAGA SEQ ID NO: 2
(signal sequence single underlined) (transmembrane domain double underlined)
<u>MLAVGCALLAALLATPGAALA</u>PGGCPAQEVARGVLTSLPGDSVTLTCPGGEPEDNATVHWVLRKPAEGSHLSRWAGVGRRLL
LRSVQLHDSGNYSCYRAGRPAATVHLLVDVPPEEPQLSCFRKSPLSNVVCEWGPRSTPSPTTKAVLLVRKFQNSPAEDFQEP
CQYSQESQKFSCQLAVPEGDSSFYIVSMCVASSVGSKLSKTQTFQGCGILQPDPPANITVTAVARNPRWLSVTWQDPHSWNS
SFYRLRFELRYRAERSKTFTTWMVKDLQHHCVIHDAWSGLRHVVQLRAQEEFGQGEWSEWSPEAMGTPWTESRSPPAENEVS
TPTQAPTTNKDDDNILSGDSANATSLPVQDSSSV<u>PLPTFLVAGGSLAFGTLLCIAIVLRFKKTWKLRALKEG</u>KTSMHPPYSL
GQLVPERPRPTPVLVPLISPPVSPSSLGSDNTSSHNRPDARDPRSPYDISNTDYFFPR SEQ ID NO: 3 (his-tagged cyno gp80)
(signal sequence single underlined) (transmembrane domain double underlined)
<u>ATGCTGGCCGTCGGCTGCGCGCTGCTGGCTGCCTTGCTGGCCACGCCGGGGGCGGCGCTG</u>CCCCGGGGGCTGCCCTGCAC
AGGAGGTGGCGAGAGGTGTGCTGACCAGTCTGCCAGGAGACAGCGTGACTCTGACCTGCCCAGGGGAGAGCCGGAAGACAA
TGCCACTGTTCACTGGGTTCTCAGGAAGCCAGCTGAAGGCTCCCACCTCAGCAGATGGGCTGGCGTGGGAAGGAGGCTGCTG
CTGAGGTCGGTGCAGCTCCATGACTCTGGAAACTATTCATGCTACCGGGCCGGCCGCCCGGCTGCAACTGTGCACTTGCTGG
TGGATGTTCCCCCCGAGGAGCCCCAGCTCTCCTGCTTCCGGAAGAGCCCACTCAGCAACGTTGTTTGTGAGTGGGGTCCTCG
GAGCACCCCATCTCCGACGACCAAGGCTGTGCTGTTGGTGAGGAAGTTTCAGAACAGTCCGGCCGAAGACTTCCAGGAGCCG
TGCCAGTATTCCCAGGAGTCCCAGAAGTTCTCCTGCCAGTTGGCAGTCCCGGAGGGAGACAGCTCTTTCTACATAGTGTCCA TABLE 4-continued Alignment of human and cyno gp80.
The predicted amino acid sequences for human (SEQ ID NO: 11) and cyno gp80
(SEQ ID NO: 2) are aligned. The cyno sequence is 97% identical to the human
sequence, respectively (divergent residues shown in bold).

```
TGTGCGTCGCCAGTAGTGTCGGGAGCAAGCTCAGCAAAACTCAGACCTTTCAGGGTTGTGGAATCTTGCAGCCTGATCCGCC
TGCCAACATCACAGTCACTGCCGTGGCCAGAAACCCCCGCTGGCTCAGTGTCACCTGGCAAGACCCCCACTCCTGGAACTCA
TCTTTCTACAGACTACGGTTTGAGCTCAGATATCGAGCTGAACGGTCAAAGACATTCACAACATGGATGGTCAAGGACCTCC
AGCATCACTGTGTCATCCACGACGCCTGGAGCGGCCTGAGGCACGTGGTGCAGCTTCGTGCCCAGGAGGAGTTCGGGCAAGG
CGAGTGGAGCGAGTGGAGCCCGGAGGCCATGGGCACGCCTTGGACAGAATCCAGGAGTCCTCCAGCTGAGAACGAGGTGTCC
ACCCCCACGCAGGCACCTACTACTAATAAAGATGATGATAATATTCTCTCCGGAGATTCTGCAAATGCGACAAGCCTCCCAG
TGCAAGATTCTTCTTCGGTACCACTGCCCACATTCCTGGTTGCTGGAGGGAGCCTGGCGTTCGGAACGCTCCTGTGCATTGC
CATTGTTCTGAGGTTCAAGAAGACGTGGAAGCTGCGGGCTCTGAAGGAAGGCAAGACATGCACCCGCCGTATTCTTTG
GGGCAGCTGGTCCCAGAGAGGCCGCGACCCACCCCAGTGCTTGTTCCTCTCATCTCCCCACCAGTGTCCCCCAGTAGCCTGG
GGTCTGACAACACCTCGAGCCACAACCGACCAGATGCCAGGGACCCACGGAGCCCTTACGACATCAGCAATACAGACTACTT
CTTCCCCAGAGGATCCCATCACCACCACCATCAC
```

SEQ ID NO: 4 (his-tagged cyno gp80) (signal sequence underlined)
<u>MLAVGCALLAALLATPGAAL</u>APGGCPAQEVARGVLTSLPGDSVTLTCPGGEPEDNATVHWVLRKPAEGSHLSRWAGVGRRLL
LRSVQLHDSGNYSCYRAGRPAATVHLLVDVPPEEPQLSCFRKSPLSNVVCEWGPRSTPSPTTKAVLLVRKFQNSPAEDFQEP
CQYSQESQKFSCQLAVPEGDSSFYIVSMCVASSVGSKLSKTQTFQGCGILQPDPPANITVTAVARNPRWLSVTWQDPHSWNS
SFYRLRFELRYRAERSKTFTTWMVKDLQHHCVIHDAWSGLRHVVQLRAQEEFGQGEWSEWSPEAMGTPWTESRSPPAENEVS
TPTQAPTTNKDDDNILGSHHHHHH SEQ ID NO: 5
(extracellular domain of mature cyno gp80) (signal sequence underlined)
<u>ATGCTGGCCGTCGGCTGCGCGCTGCTGGCTGCCTTGCTGGCCACGCCGGGGCGGCGCTGGCCCCGGGGGGCTGCCCTGCAC</u>
AGGAGGTGGCGAGAGGTGTGCTGACCAGTCTGCCAGGAGACAGCGTGACTCTGACCTGCCCAGGGGGAGAGCCGGAAGACAA
TGCCACTGTTCACTGGGTTCTCAGGAAGCCAGCTGAAGGCTCCCACCTCAGCAGATGGGCTGGCGTGGGAAGGAGGCTGCTG
CTGAGGTCGGTGCAGCTCCATGACTCTGGAAACTATTCATGCTACCGGGCCGGCCGCCCGGCTGCAACTGTGCACTTGCTGG
TGGATGTTCCCCCCGAGGAGCCCCAGCTCTCCTGCTTCCGGAAGAGCCCACTCAGCAACGTTGTTTGTGAGTGGGGTCCTCG
GAGCACCCCATCTCCGACGACCAAGGCTGTGCTGTTGGTGAGGAAGTTTCAGAACAGTCCGGCCGAAGACTTCCAGGAGCCG
TGCCAGTATTCCCAGGAGTCCCAGAAGTTCTCCTGCCAGTTGCCAGTCCCGGAGGGAGACAGCTCTTTCTACATAGTGTCCA
TGTGCGTCGCCAGTAGTGTCGGGAGCAAGCTCAGCAAAACTCAGACCTTTCAGGGTTGTGGAATCTTGCAGCCTGATCCGCC
TGCCAACATCACAGTCACTGCCGTGGCCAGAAACCCCCGCTGGCTCAGTGTCACCTGGCAAGACCCCCACTCCTGGAACTCA
TCTTTCTACAGACTACGGTTTGAGCTCAGATATCGAGCTGAACGGTCAAAGACATTCACAACATGGATGGTCAAGGACCTCC
AGCATCACTGTGTCATCCACGACGCCTGGAGCGGCCTGAGGCACGTGGTGCAGCTTCGTGCCCAGGAGGAGTTCGGGCAAGG
CGAGTGGAGCGAGTGGAGCCCGGAGGCCATGGGCACGCCTTGGACAGAATCCAGGAGTCCTCCAGCTGAGAACGAGGTGTCC
ACCCCCACGCAGGCACCTACTACTAATAAAGATGATGATAATATTCTC SEQ ID NO: 6
(extracellular domain of mature cyno gp80) (signal sequence underlined)
<u>MLAVGCALLAALLATPGAAL</u>APGGCPAQEVARGVLTSLPGDSVTLTCPGGEPEDNATVHWVLRKPAEGSHLSRWAGVGRRLL
LRSVQLHDSGNYSCYRAGRPAATVHLLVDVPPEEPQLSCFRKSPLSNVVCEWGPRSTPSPTTKAVLLVRKFQNSPAEDFQEP
CQYSQESQKFSCQLAVPEGDSSFYIVSMCVASSVGSKLSKTQTFQGCGILQPDPPANITVTAVARNPRWLSVTWQDPHSWNS
SFYRLRFELRYRAERSKTFTTWMVKDLQHHCVIHDAWSGLRHVVQLRAQEEFGQGEWSEWSPEAMGTPWTESRSPPAENEVS
TPTQAPTTNKDDDNIL SEQ ID NO: 7
(his-tagged extracellular domain of mature cyno gp80) (signal sequence underlined)
<u>ATGCTGGCCGTCGGCTGCGCGCTGCTGGCTGCCTTGCTGGCCACGCCGGGGCGGCGCTGGCCCCGGGGGGCTGCCCTGCAC</u>
AGGAGGTGGCGAGAGGTGTGCTGACCAGTCTGCCAGGAGACAGCGTGACTCTGACCTGCCCAGGGGGAGAGCCGGAAGACAA
TGCCACTGTTCACTGGGTTCTCAGGAAGCCAGCTGAAGGCTCCCACCTCAGCAGATGGGCTGGCGTGGGAAGGAGGCTGCTG
CTGAGGTCGGTGCAGCTCCATGACTCTGGAAACTATTCATGCTACCGGGCCGGCCGCCCGGCTGCAACTGTGCACTTGCTGG
TGGATGTTCCCCCCGAGGAGCCCCAGCTCTCCTGCTTCCGGAAGAGCCCACTCAGCAACGTTGTTTGTGAGTGGGGTCCTCG
GAGCACCCCATCTCCGACGACCAAGGCTGTGCTGTTGGTGAGGAAGTTTCAGAACAGTCCGGCCGAAGACTTCCAGGAGCCG
TGCCAGTATTCCCAGGAGTCCCAGAAGTTCTCCTGCCAGTTGCCAGTCCCGGAGGGAGACAGCTCTTTCTACATAGTGTCCA
TGTGCGTCGCCAGTAGTGTCGGGAGCAAGCTCAGCAAAACTCAGACCTTTCAGGGTTGTGGAATCTTGCAGCCTGATCCGCC
TGCCAACATCACAGTCACTGCCGTGGCCAGAAACCCCCGCTGGCTCAGTGTCACCTGGCAAGACCCCCACTCCTGGAACTCA
TCTTTCTACAGACTACGGTTTGAGCTCAGATATCGAGCTGAACGGTCAAAGACATTCACAACATGGATGGTCAAGGACCTCC
AGCATCACTGTGTCATCCACGACGCCTGGAGCGGCCTGAGGCACGTGGTGCAGCTTCGTGCCCAGGAGGAGTTCGGGCAAGG
CGAGTGGAGCGAGTGGAGCCCGGAGGCCATGGGCACGCCTTGGACAGAATCCAGGAGTCCTCCAGCTGAGAACGAGGTGTCC
ACCCCCACGCAGGCACCTACTACTAATAAAGATGATGATAATATTCTCGGATCCCATCACCACCACCATCAC SEQ ID NO: 8
(his-tagged extracellular domain of mature cyno gp80) (signal sequence underlined)
<u>MLAVGCALLAALLATPGAAL</u>APGGCPAQEVARGVLTSLPGDSVTLTCPGGEPEDNATVHWVLRKPAEGSHLSRWAGVGRRLL
LRSVQLHDSGNYSCYRAGRPAATVHLLVDVPPEEPQLSCFRKSPLSNVVCEWGPRSTPSPTTKAVLLVRKFQNSPAEDFQEP
CQYSQESQKFSCQLAVPEGDSSFYIVSMCVASSVGSKLSKTQTFQGCGILQPDPPANITVTAVARNPRWLSVTWQDPHSWNS
SFYRLRFELRYRAERSKTFTTWMVKDLQHHCVIHDAWSGLRHVVQLRAQEEFGQGEWSEWSPEAMGTPWTESRSPPAENEVS
TPTQAPTTNKDDDNILGSHHHHHH SEQ ID NO: 10
(mature cyno gp80 without signal sequence)
LAPGGCPAQEVARGVLTSLPGDSVTLTCPGGEPEDNATVHWVLRKPAEGSHLSRWAGVGRRLLLRSVQLHDSGNYSCYRAGR
PAATVHLLVDVPPEEPQLSCFRKSPLSNVVCEWGPRSTPSPTTKAVLLVRKFQNSPAEDFQEPCQYSQESQKFSCQLAVPEG
DSSFYIVSMCVASSVGSKLSKTQTFQGCGILQPDPPANITVTAVARNPRWLSVTWQDPHSWNSSFYRLRFELRYRAERSKTF
TTWMVKDLQHHCVIHDAWSGLRHVVQLRAQEEFGQGEWSEWSPEAMGTPWTESRSPPAENEVSTPTQAPTTNKDDDNILSGD
SANATSLPVQDSSSVPLPTFLVAGGSLAFGTLLCIAIVLRFKKTWKLRALKEGKTSMHPPYSLGQLVPERPRPTPVLVPLIS
PPVSPSSLGSDNTSSHNRPDARDPRSPYDISNTDYFFPR

TABLE 4-continued

Alignment of human and cyno gp80.
The predicted amino acid sequences for human (SEQ ID NO: 11) and cyno gp80
(SEQ ID NO: 2) are aligned. The cyno sequence is 97% identical to the human
sequence, respectively (divergent residues shown in bold).

SEQ ID NO: 11 (human gp80)
MLAVGCALLAALLAAPGAALAPRRCPAQEVARGVLTSLPGDSVTLTCPGVEPEDNATVHWVLRKPAAGSHPSRWAGMGRRLL
LRSVQLHDSGNYSCYRAGRPAGTVHLLVDVPPEEPQLSCFRKSPLSNVVCEWGPRSTPSLTTKAVLLVRKFQNSPAEDFQEP
CQYSQESQKFSCQLAVPEGDSSFYIVSMCVASSVGSKFSKTQTFQGCGILQPDPPANITVTAVARNPRWLSVTWQDPHSWNS
SFYRLRFELRYRAERSKTFTTWMVKDLQHHCVIHDAWSGLRHVVQLRAQEEFGQGEWSEWSPEAMGTPWTESRSPPAENEVS
TPMQALTTNKDDDNILFRDSANATSLPVQDSSSVPLPTFLVAGGSLAFGTLLCIAIVLRFKKTWKLRALKEGKTSMHPPYSL
GQLVPERPRPTPVLVPLISPPVSPSSLGSDNTSSHNRPDARDPRSPYDISNTDYFFPR SEQ ID NO: 12 (Homo sapiens)
TGAGTCATGTGCGAGTGGGAAGTCGCACTGACACTGAGCCGGGCCAGAGGGAGAGGAGCCGAGCGCGGCGCGGGGCCGAGGG
ACTCGCAGTGTGTGTAGAGAGCCGGGCTCCTGCGGATGGGGGCTGCCCCCGGGGCCTGAGCCCGCCTGCCCGCCCACCGCCC
CGCCCCGCCCCTGCCACCCCTGCCGCCCGGTTCCCATTAGCCTGTCCGCCTCTGCGGGACCATGGAGTGGTAGCCGAGGAGG
AAGCATGCTGGCCGTCGGCTGCGCGCTGCTGGCTGCCCTGCTGGCCGCGCCGGGAGCGGCGCTGGCCCCAAGGCGCTGCCCT
GCGCAGGAGGTGGCGAGAGGCGTGCTGACCAGTCTGCCAGGAGACAGCGTGACTCTGACCTGCCCGGGGGTAGAGCCGGAAG
ACAATGCCACTGTTCACTGGGTGCTCAGGAAGCCGGCTGCAGGCTCCCACCCCAGCAGATGGGCTGGCATGGGAAGGAGGCT
GCTGCTGAGGTCGGTGCAGCTCCACGACTCTGGAAACTATTCATGCTACCGGGCCGGCCGCCCAGCTGGGACTGTGCACTTG
CTGGTGGATGTTCCCCCGAGGAGCCCCAGCTCTCCTGCTTCCGGAAGAGCCCCCTCAGCAATGTTGTTTGTGAGTGGGGTC
CTCGGAGCACCCCATCCCTGACGACAAAGGCTGTGCTCTTGGTGAGGAAGTTTCAGAACAGTCCGGCCGAAGACTTCCAGGA
GCCGTGCCAGTATTCCCAGGAGTCCCAGAAGTTCTCCTGCCAGTTAGCAGTCCCGGAGGGAGACAGCTCTTTCTACATAGTG
TCCATGTGCGTCGCCAGTAGTGTCGGGAGCAAGTTCAGCAAAACTCAAACCTTTCAGGGTTGTGGAATCTTGCAGCCTGATC
CGCCTGCCAACATCACAGTCACTGCCGTGGCCAGAAACCCCGCTGGCTCAGTGTCACCTGGCAAGACCCCCACTCCTGGAA
CTCATCTTTCTACAGACTACGGTTTGAGCTCAGATATCGGGCTGAACGGTCAAAGACATTCACAACATGGATGGTCAAGGAC
CTCCAGCATCACTGTGTCATCCACGACGCCTGGAGCGGCCTGAGGCACGTGGTGCAGCTTCGTGCCCAGGAGGAGTTCGGGC
AAGGCGAGTGGAGCGAGTGGAGCCCGGAGGCCATGGGCACGCCTTGGACAGAATCCAGGAGTCCTCCAGCTGAGAACGAGGT
GTCCACCCCCATGCAGGCACTTACTACTAATAAAGACGATGATAATATTCTCTTCAGAGATTCTGCAAATGCGACAAGCCTC
CCAGTGCAAGATTCTTCTTCAGTACCACTGCCCACATTCCTGGTTGCTGGAGGGAGCCTGGCCTTCGGAACGCTCCTCTGCA
TTGCCATTGTTCTGAGGTTCAAGAAGACGTGGAAGCTGCGGGCTCTGAAGGAAGGCAAGACAAGCATGCATCCGCCGTACTC
TTTGGGGCAGCTGGTCCCGGAGAGGCCTCGACCCACCCCAGTGCTTGTTCCTCTCATCTCCCCACCGGTGTCCCCCAGCAGC
CTGGGGTCTGACAATACCTCGAGCCACAACCGACCAGATGCCAGGGACCCACGGAGCCCTTATGACATCAGCAATACAGACT
ACTTCTTCCCCAGATAGCTGGCTGGGTGGCACCAGCAGCCTGGACCCTGTGGATGATAAAACACAAACGGGCTCAGCA

---

What is claimed:

1. An isolated polypeptide comprising a peptide chain having the amino acid sequence set forth in SEQ ID NO:2.

2. An isolated polypeptide comprising a peptide chain encoded by the nucleotide sequence set forth in SEQ ID NO:1.

3. An isolated polypeptide comprising a peptide chain having the amino acid sequence set forth in SEQ ID NO:6.

4. An isolated polypeptide comprising a peptide chain encoded by the nucleotide sequence set forth in SEQ ID NO:5.

5. An isolated polypeptide comprising a peptide chain having the amino acid sequence set forth in SEQ ID NO:10.

6. A peptide chain produced by a method for expressing a peptide chain comprising the steps of:
   (a) providing an RNA coding for a peptide chain having an amino acid sequence selected from the group consisting of SEQ ID NOS:2, 6, and 10;
   (b) providing the components of a cell-free expression system;
   (c) initiating cell free expression from the RNA provided; and
   (d) recovering the peptide chain.

7. The peptide chain of claim 6, wherein the method further comprises, after the recovering step, confirming expression of a peptide chain comprising the amino acid sequence selected from the group consisting of SEQ ID NOS:2, 6, and 10.

8. The peptide chain of claim 7, wherein the cell-free expression system is selected from the group consisting of a reticulocyte lystate-based expression system, a wheat germ extract-based expression system, and an *Escherichia coli* extract-based expression system.

9. A method for assessing the safety of a therapeutic candidate through the use of a gp80 therapeutic candidate comprising:
   a) providing a gp80 therapeutic candidate, a first cynomolgus monkey, a second cynomolgus monkey, wherein the gp80 therapeutic candidate is an antibody to cyno gp80, an antibody fragment to cyno gp80, or a combination of the antibody and the antibody fragment, and wherein the antibody, antibody fragment, or combination is directed to the cyno gp80 sequence comprising the amino acid sequence of a member from the group consisting of SEQ ID NOS: 2, 6, and 10;
   b) administering the gp80 therapeutic candidate to the first cynomolgus monkey; and
   c) determining whether the first cynomolgus monkey is presenting a deleterious symptom relative to the second monkey, wherein presentation of a deleterious symptom by the first cynomolgus monkey shows the gp80 therapeutic candidate is unsafe, and lack of presentation of a deleterious symptom by the first cynomolgus monkey shows the gp80 therapeutic candidate is safe.

\* \* \* \* \*

SEQUENCE LISTING

<160> NUMBER OF SEQ ID NOS: 13

<210> SEQ ID NO 1
<211> LENGTH: 1404
<212> TYPE: DNA
<213> ORGANISM: Macaca fascicularis

<400> SEQUENCE: 1

| | | | | | |
|---|---|---|---|---|---|
| atgctggccg | tcggctgcgc | gctgctggct | gccttgctgg | ccacgccggg | ggcggcgctg | 60 |
| gccccggggg | gctgccctgc | acaggaggtg | gcgagaggtg | tgctgaccag | tctgccagga | 120 |
| gacagcgtga | ctctgacctg | cccaggggga | gagccggaag | acaatgccac | tgttcactgg | 180 |
| gttctcagga | agccagctga | aggctcccac | ctcagcagat | gggctggcgt | gggaaggagg | 240 |
| ctgctgctga | ggtcggtgca | gctccatgac | tctggaaact | attcatgcta | ccgggccggc | 300 |
| cgcccggctg | caactgtgca | cttgctggtg | gatgttcccc | ccgaggagcc | ccagctctcc | 360 |
| tgcttccgga | agagcccact | cagcaacgtt | gtttgtgagt | gggtcctcg | gagcacccca | 420 |
| tctccgacga | ccaaggctgt | gctgttggtg | aggaagtttc | agaacagtcc | ggccgaagac | 480 |
| ttccaggagc | cgtgccagta | ttcccaggag | tcccagaagt | tctcctgcca | gttggcagtc | 540 |
| ccggagggag | acagctcttt | ctacatagtg | tccatgtgcg | tcgccagtag | tgtcgggagc | 600 |
| aagctcagca | aaactcagac | ctttcagggt | tgtggaatct | tgcagcctga | tccgcctgcc | 660 |
| aacatcacag | tcactgccgt | ggccagaaac | cccgctggc | tcagtgtcac | ctggcaagac | 720 |
| ccccactcct | ggaactcatc | tttctacaga | ctacggtttg | agctcagata | tcgagctgaa | 780 |

```
cggtcaaaga cattcacaac atggatggtc aaggacctcc agcatcactg tgtcatccac    840
gacgcctgga gcggcctgag gcacgtggtg cagcttcgtg cccaggagga gttcgggcaa    900
ggcgagtgga gcgagtggag cccggaggcc atgggcacgc cttggacaga atccaggagt    960
cctccagctg agaacgaggt gtccacccc acgcaggcac ctactactaa taaagatgat   1020
gataatattc tctccggaga ttctgcaaat gcgacaagcc tcccagtgca agattcttct   1080
tcggtaccac tgcccacatt cctggttgct ggagggagcc tggcgttcgg aacgctcctg   1140
tgcattgcca ttgttctgag gttcaagaag acgtggaagc tgcgggctct gaaggaaggc   1200
aagacaagca tgcacccgcc gtattctttg gggcagctgg tcccagagag ccgcgaccc   1260 accccagtgc ttgttcctct catctcccca ccagtgtccc ccagtagcct ggggtctgac   1320
aacacctcga gccacaaccg accagatgcc agggacccac ggagcccttta cgacatcagc   1380 aatacagact acttcttccc caga                                          1404
```

<210> SEQ ID NO 2
<211> LENGTH: 468
<212> TYPE: PRT
<213> ORGANISM: Macaca fascicularis

<400> SEQUENCE: 2

```
Met Leu Ala Val Gly Cys Ala Leu Leu Ala Leu Leu Ala Thr Pro
 1               5                  10                  15

Gly Ala Ala Leu Ala Pro Gly Gly Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Gly Glu Pro Glu Asp Asn Ala Thr Val His Trp Val Leu Arg Lys
    50                  55                  60

Pro Ala Glu Gly Ser His Leu Ser Arg Trp Ala Gly Val Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Ala Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Pro Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Leu Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270
```

```
Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
            290                 295                 300

Glu Trp Ser Pro Glu Ala Met Gly Thr Pro Thr Glu Ser Arg Ser
305                 310                 315                 320

Pro Pro Ala Glu Asn Glu Val Ser Thr Pro Gln Ala Pro Thr Thr
                325                 330                 335

Asn Lys Asp Asp Asp Asn Ile Leu Ser Gly Asp Ser Ala Asn Ala Thr
            340                 345                 350

Ser Leu Pro Val Gln Asp Ser Ser Val Pro Leu Pro Thr Phe Leu
            355                 360                 365

Val Ala Gly Gly Ser Leu Ala Phe Gly Thr Leu Leu Cys Ile Ala Ile
            370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 3
<211> LENGTH: 1428
<212> TYPE: DNA
<213> ORGANISM: Macaca fascicularis

<400> SEQUENCE: 3
atgctggccg tcggctgcgc gctgctggct gccttgctgg ccacgccggg ggcggcgctg      60
gccccggggg gctgccctgc acaggaggtg gcgagaggtg tgctgaccag tctgccagga     120
gacagcgtga ctctgacctg cccaggggga gagccggaag acaatgccac tgttcactgg     180
gttctcagga agccagctga aggctcccac ctcagcagat gggctggcgt gggaaggagg     240
ctgctgctga ggtcggtgca gctccatgac tctggaaact attcatgcta ccgggccggc     300
cgcccggctg caactgtgca cttgctggtg atgttccccc cgaggagccc cagctctcc     360 tgcttccgga gagcccact cagcaacgtt gtttgtgagt ggggtcctcg gagcacccca     420
tctccgacga ccaaggctgt gctgttggtg aggaagtttc agaacagtcc ggccgaagac     480
ttccaggagc cgtgccagta ttcccaggag tcccagaagt ctcctgcca gttggcagtc     540 ccggagggag acagctcttt ctacatagtg tccatgtgcg tcgccagtag tgtcgggagc     600
aagctcagca aaactcagac ctttcagggt tgtggaatct tgcagcctga tccgcctgcc     660
aacatcacag tcactgccgt ggccagaaac ccccgctggc tcagtgtcac ctggcaagac     720
ccccactcct ggaactcatc tttctacaga ctacggtttg agctcagata tcgagctgaa     780
cggtcaaaga cattcacaac atggatggtc aaggacctcc agcatactg tgtcatccac     840 gacgcctgga gcggcctgag gcacgtggtg cagcttcgtg cccaggagga gttcgggcaa     900
ggcgagtgga gcgagtggag cccggaggcc atgggcacgc cttggacaga atccaggagt     960
```

-continued

```
cctccagctg agaacgaggt gtccacccccc acgcaggcac ctactactaa taaagatgat    1020
gataatattc tctccggaga ttctgcaaat gcgacaagcc tcccagtgca agattcttct    1080
tcggtaccac tgcccacatt cctggttgct ggagggagcc tggcgttcgg aacgctcctg    1140
tgcattgcca ttgttctgag gttcaagaag acgtggaagc tgcgggctct gaaggaaggc    1200
aagacaagca tgcacccgcc gtattctttg gggcagctgg tcccagagag gccgcgaccc    1260
accccagtgc ttgttcctct catctcccca ccagtgtccc ccagtagcct ggggtctgac    1320
aacacctcga gccacaaccg accagatgcc agggacccac ggagcccttta cgacatcagc    1380 aatacagact acttcttccc cagaggatcc catcaccacc accatcac                 1428
```

<210> SEQ ID NO 4
<211> LENGTH: 352
<212> TYPE: PRT
<213> ORGANISM: Macaca fascicularis

<400> SEQUENCE: 4

```
Met Leu Ala Val Gly Cys Ala Leu Leu Ala Leu Leu Ala Thr Pro
 1               5                   10                  15

Gly Ala Ala Leu Ala Pro Gly Gly Cys Pro Ala Gln Glu Val Ala Arg
                20                  25                  30

Gly Val Leu Thr Ser Leu Pro Gly Asp Ser Val Thr Leu Thr Cys Pro
                35                  40                  45

Gly Gly Glu Pro Glu Asp Asn Ala Thr Val His Trp Val Leu Arg Lys
         50                  55                  60

Pro Ala Glu Gly Ser His Leu Ser Arg Trp Ala Gly Val Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Ala Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Pro Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Leu Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
```

```
                290                 295                 300
Glu Trp Ser Pro Glu Ala Met Gly Thr Pro Trp Thr Glu Ser Arg Ser
305                 310                 315                 320

Pro Pro Ala Glu Asn Glu Val Ser Thr Pro Thr Gln Ala Pro Thr Thr
                325                 330                 335

Asn Lys Asp Asp Asp Asn Ile Leu Gly Ser His His His His His His
                340                 345                 350

<210> SEQ ID NO 5
<211> LENGTH: 1032
<212> TYPE: DNA
<213> ORGANISM: Macaca fascicularis

<400> SEQUENCE: 5
atgctggccg tcggctgcgc gctgctggct gccttgctgg ccacgccggg ggcggcgctg     60
gccccggggg gctgcccctgc acaggaggtg gcgagaggtg tgctgaccag tctgccagga    120
gacagcgtga ctctgacctg cccaggggga gagccggaag acaatgccac tgttcactgg    180
gttctcagga agccagctga aggctcccac ctcagcagat gggctggcgt gggaaggagg    240
ctgctgctga ggtcggtgca gctccatgac tctggaaact attcatgcta ccgggccggc    300
cgcccggctg caactgtgca cttgctggtg atgttcccc cgaggagcc ccagctctcc     360 tgcttccgga gagcccact cagcaacgtt gtttgtgagt ggggtcctcg gagcacccca    420
tctccgacga ccaaggctgt gctgttggtg aggaagtttc agaacagtcc ggccgaagac    480
ttccaggagc cgtgccagta ttcccaggag tcccagaagt tctcctgcca gttggcagtc    540
ccggagggag acagctcttt ctacatagtg tccatgtgcg tcgccagtag tgtcgggagc    600
aagctcagca aaactcagac cttttcaggg tgtggaatct tgcagcctga tccgcctgcc    660
aacatcacag tcactgccgt ggccagaaac ccccgctggc tcagtgtcac ctggcaagac    720
ccccactcct ggaactcatc tttctacaga ctacggtttg agctcagata tcgagctgaa    780
cggtcaaaga cattcacaac atggatggtc aaggacctcc agcatcactg tgtcatccac    840
gacgcctgga gcggcctgag gcacgtggtg cagcttcgtg cccaggagga gttcgggcaa    900
ggcgagtgga gcgagtggag cccggaggcc atgggcacgc cttggacaga atccaggagt    960
cctccagctg agaacgaggt gtccaccccc acgcaggcac tactactaa taaagatgat   1020 gataatattc tc                                                      1032

<210> SEQ ID NO 6
<211> LENGTH: 344
<212> TYPE: PRT
<213> ORGANISM: Macaca fascicularis

<400> SEQUENCE: 6

Met Leu Ala Val Gly Cys Ala Leu Leu Ala Ala Leu Leu Ala Thr Pro
1               5                   10                  15

Gly Ala Ala Leu Ala Pro Gly Gly Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Gly Glu Pro Glu Asp Asn Ala Thr Val His Trp Val Leu Arg Lys
        50                  55                  60

Pro Ala Glu Gly Ser His Leu Ser Arg Trp Ala Gly Val Gly Arg Arg
65                  70                  75                  80

Leu Leu Leu Arg Ser Val Gln Leu His Asp Ser Gly Asn Tyr Ser Cys
                85                  90                  95
```

```
Tyr Arg Ala Gly Arg Pro Ala Ala Thr Val His Leu Leu Val Asp Val
                100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Pro Thr Thr
        130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Leu Ser Lys Thr Gln Thr Phe
        195                 200                 205
Gln Gly Cys Gly Ile Leu Gln Pro Asp Pro Pro Ala Asn Ile Thr Val
    210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
        275                 280                 285
Val Val Gln Leu Arg Ala Gln Glu Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Gln Ala Pro Thr Thr
                325                 330                 335
Asn Lys Asp Asp Asp Asn Ile Leu
            340

<210> SEQ ID NO 7
<211> LENGTH: 1056
<212> TYPE: DNA
<213> ORGANISM: Macaca fascicularis

<400> SEQUENCE: 7
atgctggccg tcggctgcgc gctgctggct gccttgctgg ccacgccggg ggcggcgctg      60
gccccggggg gctgccctgc acaggaggtg gcgagaggtg tgctgaccag tctgccagga     120
gacagcgtga ctctgacctg cccaggggga gagccggaag acaatgccac tgttcactgg     180
gttctcagga agccagctga aggctcccac ctcagcagat gggctggcgt gggaaggagg     240
ctgctgctga ggtcggtgca gctccatgac tctggaaact attcatgcta ccgggccggc     300
cgcccggctg caactgtgca cttgctggtg gatgttcccc cgaggagcc  ccagctctcc     360 tgcttccgga gagcccact cagcaacgtt gtttgtgagt ggggtcctcg gagcacccca     420
tctccgacga ccaaggctgt gctgttggtg aggaagtttc agaacagtcc ggccgaagac     480
ttccaggagc cgtgccagta ttcccaggag tcccagaagt tctcctgcca gttggcagtc     540
ccggagggag acagctcttt ctacatagtg tccatgtgcg tcgccagtag tgtcgggagc     600
aagctcagca aaactcagac ctttcagggt tgtggaatct gcagcctga tccgcctgcc     660 aacatcacag tcactgccgt ggccagaaac ccccgctggc tcagtgtcac ctggcaagac     720
```

```
cccactcct ggaactcatc tttctacaga ctacggtttg agctcagata tcgagctgaa    780
cggtcaaaga cattcacaac atggatggtc aaggacctcc agcatcactg tgtcatccac    840
gacgcctgga gcggcctgag gcacgtggtg cagcttcgtg cccaggagga gttcgggcaa    900
ggcgagtgga gcgagtggag cccggaggcc atgggcacgc cttggacaga atccaggagt    960
cctccagctg agaacgaggt gtccaccccc acgcaggcac ctactactaa taaagatgat   1020
gataatattc tcggatccca tcaccaccac catcac                              1056

<210> SEQ ID NO 8
<211> LENGTH: 352
<212> TYPE: PRT
<213> ORGANISM: Macaca fascicularis

<400> SEQUENCE: 8

Met Leu Ala Val Gly Cys Ala Leu Leu Ala Leu Leu Ala Thr Pro
1               5                   10                  15

Gly Ala Ala Leu Ala Pro Gly Gly Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Gly Glu Pro Glu Asp Asn Ala Thr Val His Trp Val Leu Arg Lys
    50                  55                  60

Pro Ala Glu Gly Ser His Leu Ser Arg Trp Ala Gly Val Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Ala Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Pro Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Leu Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320
```

Pro Pro Ala Glu Asn Glu Val Ser Thr Pro Thr Gln Ala Pro Thr Thr
            325                 330                 335

Asn Lys Asp Asp Asp Asn Ile Leu Gly Ser His His His His His
            340                 345                 350

<210> SEQ ID NO 9
<211> LENGTH: 5920
<212> TYPE: DNA
<213> ORGANISM: Macaca mulatta

<400> SEQUENCE: 9

| | | | | | |
|---|---|---|---|---|---|
| ggcggtcccc | tgttctcccc | gctcaggtgc | ggcgctgtgg | caggaagcca | ccccctcggt | 60 |
| cggccggtgc | gcggggctgt | tgcgccatcc | gctccagctt | tcgtaaccgc | accctgggac | 120 |
| ggcccagaga | cgctccagcg | cgagttcctc | aaatgttttc | ctgtgttgcc | aggaccgtcc | 180 |
| gccgctctga | gtcatgtgcg | agtgggaagt | ctcactgaca | ctgagaccgg | ccagtgggag | 240 |
| cggagccgag | cgcggcgcgg | ggctgaggga | ctcgcagtgt | atatagagcg | ccgggctcct | 300 |
| gcgatggggg | ctgcccccgg | agactgagcc | agcctgcccg | cccaccgccc | cgcccctgcc | 360 |
| gcccggttcc | caccagcctg | tccgcctctg | cgggaccatg | gagcggtagc | cgaggaggaa | 420 |
| gcatgctggc | cgtcggctgc | gcgctgctgg | ctgccctgct | ggccgcgccg | gggcggcgc | 480 |
| tggccccggg | gggctgccct | gcgcaggagg | tggcgagagg | tgtgctgacc | agtctgccag | 540 |
| agacagcgt | gactctgacc | tgcccagggg | gagagccgga | agacaatgcc | actgttcact | 600 |
| gggttctcag | gaagccagct | gtaggctccc | acctcagcag | atgggctggc | gtgggaagga | 660 |
| ggctgctgct | gaggtcggtg | cagctccatg | actctggaaa | ctattcatgc | taccgggccg | 720 |
| gccgccggc | tggaactgtg | cacttgctgg | tggatgttcc | ccccgaggag | ccccagctct | 780 |
| cctgcttccg | gaagagcccc | ctcagcaacg | ttgtttgtga | gtggggtcct | cggagcaccc | 840 |
| catctccgac | gaccaaggct | gtgctgttgg | tgaggaagtt | tcagaacagt | ccggccgaag | 900 |
| acttccagga | gccgtgccag | tattcccagg | agtcccagaa | gttctcctgc | cagttggcag | 960 |
| tcccggaggg | agacagctct | ttctacatag | tgtccatgtg | cgtcgccagt | agtgtcggga | 1020 |
| gcaagctcag | caaaactcag | acctttcagg | gttgtggaat | cttgcagcct | gatccgcctg | 1080 |
| ccaacatcac | agtcactgcc | gtggccagaa | accccgctg | gctcagtgtc | acctggcaag | 1140 |
| acccccactc | ctggaactca | tctttctaca | gactacggtt | tgagctcaga | tatcgagctg | 1200 |
| aacggtcaaa | gacattcaca | acatggatgg | tcaaggacct | ccagcatcac | tgtgtcatcc | 1260 |
| acgacgcctg | gagcggcctg | aggcacgtgg | tgcagcttcg | tgcccaggag | gagttcgggc | 1320 |
| aaggcgagtg | gagcgagtgg | agcccggagg | ccatgggcac | gccttggaca | gaatccagga | 1380 |
| gtcctccagc | tgagaacgag | gtgtccaccc | ccacgcaggc | acctactact | aataaagatg | 1440 |
| atgataatat | tctctccaga | gattctgcaa | atgcgacaag | cctcccagtg | caagattctt | 1500 |
| cttcggtacc | actgcccaca | ttcctggttg | ctggaggag | cctggcgttc | ggaacgctcc | 1560 |
| tgtgcattgc | cattgttctg | aggttcaaga | agacgtggaa | gctgcgggct | ctgaaggaag | 1620 |
| gcaagacaag | catgcacccg | ccgtattctt | tggggcagct | ggtcccagag | aggccgcgac | 1680 |
| ccacccagt | gcttgttcct | ctcatctccc | caccagtgtc | cccagcagc | ctggggtctg | 1740 |
| acaacacctc | gagccacaac | cgaccagatg | ccagggaccc | acgagccct | tacgacatca | 1800 |
| gcaatacaga | ctacttcttc | cccagatagt | tggccagggg | gcactagcag | gctggaccct | 1860 |
| gtggatgaca | gagcacaaac | gggctcagca | aaggatgctt | cttactgcca | tgccagctta | 1920 |
| tctcagggga | gtggggcctt | tggcttcacg | gaagagcctt | gcggaaggtt | cgacaccagg | 1980 |

```
ggaaaatcag cctgctccag ctgttcagct ggttgagatt tcaaacctcc ctttccaaat    2040
gtctggctta aaggggttag agtgaacttg ggccactgtg aagagaagca tgtcaagact    2100
ctttggacat tcaacacgga cactcaaaag ctgggcagct tggtggggc ctcagtgtgg     2160 agaagcggct ggcagcccac cccccaacac ctctgcacaa gctgcgccct caggcagggg    2220
gggcggattt ccagccaaag cctccttcag ccgccacgct cctggcccac tgcatcattt    2280
catcttccag ctcaaactcc taaaacccaa gtgcctttgc aaattctgtt tttctgagcc    2340
tggggacggc ttttacttaa accgccaagg ctggggaaag aagctctctc ctccctttct    2400
tccccacagt tgaaaaacag ctgagggtgg gtgggtgaat aatacagtat ctcagggcct    2460
ggtcgttttc aacggaatta taattagttc ctcattagca ttttgctaaa tgtgaatgat    2520
aatcctaggc atttgctgaa tacagaggca actgcattgg ctttgggttg caggacctca    2580
ggtgagaagc agaggaagga gaggagaggg gcacagggtc tccaccatcc cctgtagagt    2640
gggagctgcg cggggggatca cagcctctga aaaccaatgt tctctgttct ccacctccca   2700
caaaggagag ctggcagcag ggagggcttc tgccagtgct gagatcaaaa ctgttttact    2760
gcagctttgt ttgttgtcag ccgaacctgg gtaactaggg aagataatat taaggaagac   2820
aatgtgaaaa gaaaaatgag cccggcaaga atgcatttta acttggtttt taaaaaactg    2880
ctgactgttt tctcttgaga gggtggaata tccaatatgc gctgtgtcag catagaagta    2940
acttacttag gtgtgggga agcaccataa cttttgtttag cccaaaacta agtcaagtga    3000
aaaaggagga agagaaataa tattttttcct gccaggcatg gtggttcacg cctgtaatcc    3060
cagcactctg ggaggtcgag gcgggacgat cacttgagtc caggagtttg agaccagcct    3120
gggcaatgtg gtaaaacctc atctcgacaa aaagcataaa aattagccag gtatggtaga    3180
gtgcacctga agtcccagtt agttgggagg ctgaggtggg aggatctctt gagcctggga    3240
ggtcaaggct gcagtgagcc gagattgcac cactgcactc cagcctgggt gactgagcaa    3300
gtgagaccct gtctcaaaaa agaaaaggaa aagaaaaga aaaatatttt tccctgttag     3360
agaagagatt gtggtttcat tgtgtatttt gtttttgtct taaaaagtgg aaaaatagcc    3420
tgcctcttct ctactctagg gaaaaaccag tgtgtgacta ctcccccagg cggttatgga    3480
gagggcgtcc ggtccctgtc ccagtgctga aagggagcc tcccacgact acccggcagg     3540
gtcctagaaa ttccccaccc tgaaagccct gagccttctg ctatcaaagg ggcaggtaaa    3600
aatcccattt aaaaaaaatc ccttacctcg gtgccttcct ctttttattt agctccttga    3660
gttgattcag ctctgcaaga attgaagcag aactaaatgt ctaattgtaa caccgtgatt    3720
aaccacttca gctgacttttt ctgcccgagc tttgaaaatt cagtggtgtt agtggttacc   3780
cagttagctc tcaagttatc agggtactcc acagcgggga tataccagac cacaaaacct    3840
ttctaatact ctaccctctt agaaaaacag ccaccatcac cagacaggtg caaaaggagg    3900
aaagtgacca tgttttgttt accgttttcc aggtttaagc tgttactgtc ttcagcaagc    3960
cgtgcttttc attgctgggt ttgtctgtag attttagacc ctattgctgc ttgaggcacc    4020
tcatcttaag ttggcaaaaa ggcaggacgg ctgggtgtgg tggctcacgc ctgtaatcct    4080
agcactttgg gaggccgagg tgggaggatt gcttgagctc aggaatttga gaccaacctg    4140
ggtaacatag tgagatacca tctctattat aaacaataac atttaaggaa aaaaaaggc    4200 aggcaggtgg ttatggtggt tccctcccat cctgctgcat aaagtttctg agacttgaga    4260
acagcaaaaa tgctgttaaa gggaaatatt aagaatgaga atctgcatga agggtgatta    4320
tgtgcccaca gttaattctt tataccgttt tacccacatg tggtattacc gaagccgggc    4380
```

```
agaaccatgc tagcggaaga tatgaaattc agatagctca ttattgccaa gagctaggca    4440
gctttgatct ccaaattgtt attgctttca tttttattgt aatggaactg ctttttttt     4500 ttttttttt tttttttgctt ttttttctt gttttgtttt tgtagtgaag agggttttt      4560 tccctttatt tttcataagc tactgtaaat gaagaaaaag tgtcttctct gggctgtagg    4620
cctggctcag tgtacacagg tatacatcct aagctctctc tgttctctaa tttgtggtga    4680
ctgaatatgt gtcgcaatcc acggggcatt tctacctgta tttctgcagc accccccactg   4740 ccttgagtcc ccagcagtgc tgttatttgc ctaatacctg tagccatctg ccacacagcc    4800
agacatgaaa cgctgggaca gagaccattt agattaaata caacagctta tcttgctggg    4860
tggggaaagt aaaaaatatg ctggttcaag gtctaaagta aaatgataaa taatgtttgt    4920
agcattaatg aaatattttc aagaaatgtg tccgggggta gcattggcta tgctgacgag    4980
gcctttggta actcagaaag ctcttggccc cgatggcgac ttgcccttgc actttcttta    5040
tcaggctctg agctcacacg gagcctctgg catttccctg ctgtcttggg agaaaggaaa    5100
ctggttgtgg cggcagggtg tggaatctgc tgctggaacc aggctggaag cccacctggt    5160
agtgaacagg gcccagcggg gcaggctagg agtgttgtgg tctatgggtt tgtgtcctgg    5220
agaatgttca agaatgtctt cttggctgct ttggtgctga gctctgttat ctcacagcac    5280
gtcctgaagg ctaacccagg tggggaggat gctgacacca gctccaggtg gagttggtga    5340
gaaatctgtc ttaacttgga gatgcagggg caacctgtga cccctttgagg caagagccct   5400 gcacccagct gtcccgtgca gccgtgggca ggggctgca catggagggg caggcgggcc     5460
agttcagggc cagttcagtg ccctgtaagg gcccttcagc ctcctgtcct ctgtgcggct    5520
gggcgccagc accagggagt ttctatggca accttagtga ttattaagga acattgtcag    5580
ttttatgaac atatgctcaa atgaaattct actttaggag gaaaggattg gaacagcatg    5640
ttgcaaggct gttaattaac agagagacct tattggatgg agatcacatc tgttaaatag    5700
aatacctcaa ctctacgttg ttttcttgga gataaataat agtttcaagt ttttgtttgt    5760
ttgttttacc taattacctg aaagcaaata ccaaaggctg atgtctgtat atggggcaaa    5820
gggtcagtat attttttcagt gttttttttt cttttacaag ctattttgca tttaaagtga    5880
acattgtaaa tgtttgtaat aaatgatttt taaaaataca                           5920
```

<210> SEQ ID NO 10
<211> LENGTH: 449
<212> TYPE: PRT
<213> ORGANISM: Macaca fascicularis

<400> SEQUENCE: 10

```
Leu Ala Pro Gly Gly Cys Pro Ala Gln Glu Val Ala Arg Gly Val Leu
  1               5                  10                  15

Thr Ser Leu Pro Gly Asp Ser Val Thr Leu Thr Cys Pro Gly Gly Glu
             20                  25                  30

Pro Glu Asp Asn Ala Thr Val His Trp Val Leu Arg Lys Pro Ala Glu
         35                  40                  45

Gly Ser His Leu Ser Arg Trp Ala Gly Val Gly Arg Arg Leu Leu Leu
     50                  55                  60

Arg Ser Val Gln Leu His Asp Ser Gly Asn Tyr Ser Cys Tyr Arg Ala
 65                  70                  75                  80

Gly Arg Pro Ala Ala Thr Val His Leu Leu Val Asp Val Pro Pro Glu
                 85                  90                  95

Glu Pro Gln Leu Ser Cys Phe Arg Lys Ser Pro Leu Ser Asn Val Val
```

```
              100                 105                 110
Cys Glu Trp Gly Pro Arg Ser Thr Pro Ser Pro Thr Thr Lys Ala Val
            115                 120                 125

Leu Leu Val Arg Lys Phe Gln Asn Ser Pro Ala Glu Asp Phe Gln Glu
        130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Leu Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
290                 295                 300

Glu Asn Glu Val Ser Thr Pro Thr Gln Ala Pro Thr Thr Asn Lys Asp
305                 310                 315                 320

Asp Asp Asn Ile Leu Ser Gly Asp Ser Ala Asn Ala Thr Ser Leu Pro
                325                 330                 335

Val Gln Asp Ser Ser Ser Val Pro Leu Pro Thr Phe Leu Val Ala Gly
            340                 345                 350

Gly Ser Leu Ala Phe Gly Thr Leu Leu Cys Ile Ala Ile Val Leu Arg
        355                 360                 365

Phe Lys Lys Thr Trp Lys Leu Arg Ala Leu Lys Glu Gly Lys Thr Ser
370                 375                 380

Met His Pro Pro Tyr Ser Leu Gly Gln Leu Val Pro Glu Arg Pro Arg
385                 390                 395                 400

Pro Thr Pro Val Leu Val Pro Leu Ile Ser Pro Pro Val Ser Pro Ser
                405                 410                 415

Ser Leu Gly Ser Asp Asn Thr Ser Ser His Asn Arg Pro Asp Ala Arg
            420                 425                 430

Asp Pro Arg Ser Pro Tyr Asp Ile Ser Asn Thr Asp Tyr Phe Phe Pro
        435                 440                 445

Arg

<210> SEQ ID NO 11
<211> LENGTH: 468
<212> TYPE: PRT
<213> ORGANISM: Homo sapiens

<400> SEQUENCE: 11

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30
```

```
Gly Val Leu Thr Ser Leu Pro Gly Asp Ser Val Thr Leu Thr Cys Pro
             35                  40                  45
Gly Val Glu Pro Glu Asp Asn Ala Thr Val His Trp Val Leu Arg Lys
 50                  55                  60
Pro Ala Ala Gly Ser His Pro Ser Arg Trp Ala Gly Met Gly Arg Arg
 65                  70                  75                  80
Leu Leu Leu Arg Ser Val Gln Leu His Asp Ser Gly Asn Tyr Ser Cys
                 85                  90                  95
Tyr Arg Ala Gly Arg Pro Ala Gly Thr Val His Leu Leu Val Asp Val
                100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
        130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
        195                 200                 205
Gln Gly Cys Gly Ile Leu Gln Pro Asp Pro Pro Ala Asn Ile Thr Val
    210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
        275                 280                 285
Val Val Gln Leu Arg Ala Gln Glu Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
            340                 345                 350
Ser Leu Pro Val Gln Asp Ser Ser Val Pro Leu Pro Thr Phe Leu
        355                 360                 365
Val Ala Gly Gly Ser Leu Ala Phe Gly Thr Leu Leu Cys Ile Ala Ile
    370                 375                 380
Val Leu Arg Phe Lys Lys Thr Trp Lys Leu Arg Ala Leu Lys Glu Gly
385                 390                 395                 400
Lys Thr Ser Met His Pro Pro Tyr Ser Leu Gly Gln Leu Val Pro Glu
                405                 410                 415
Arg Pro Arg Pro Thr Pro Val Leu Val Pro Leu Ile Ser Pro Pro Val
            420                 425                 430
Ser Pro Ser Ser Leu Gly Ser Asp Asn Thr Ser Ser His Asn Arg Pro
        435                 440                 445
Asp Ala Arg Asp Pro Arg Ser Pro Tyr Asp Ile Ser Asn Thr Asp Tyr
```

Phe Phe Pro Arg
465

<210> SEQ ID NO 12
<211> LENGTH: 1718
<212> TYPE: DNA
<213> ORGANISM: Homo sapiens

<400> SEQUENCE: 12

```
tgagtcatgt gcgagtggga agtcgcactg acactgagcc gggccagagg gagaggagcc      60
gagcgcggcg cggggccgag ggactcgcag tgtgtgtaga gagccgggct cctgcggatg     120
ggggctgccc ccggggcctg agcccgcctg cccgcccacc gccccgcccc gccctgcca     180
cccctgccgc ccggttccca ttagcctgtc cgcctctgcg ggaccatgga gtggtagccg     240
aggaggaagc atgctggccg tcggctgcgc gctgctggct gccctgctgg ccgcgccggg     300
agcggcgctg gcccccaagg cgctgccctg cgcaggaggtg gcgagaggcg tgctgaccag     360
tctgccagga gacagcgtga ctctgacctg cccgggggta gagccggaag acaatgccac     420
tgttcactgg gtgctcagga gccggctgc aggctcccac cccagcagat gggctggcat     480
gggaaggagg ctgctgctga ggtcggtgca gctccacgac tctggaaact attcatgcta     540
ccgggccggc cgcccagctg ggactgtgca cttgctggtg gatgttcccc ccgaggagcc     600
ccagctctcc tgcttccgga gagccccct cagcaatgtt gtttgtgagt ggggtcctcg     660
gagcacccca tccctgacga caaggcctgt gctcttggtg aggaagtttc agaacagtcc     720
ggccgaagac ttccaggagc cgtgccagta ttcccaggag tcccagaagt ctcctgcca     780
gttagcagtc ccggagggag acagctcttt ctacatagtg tccatgtgcg tcgccagtag     840
tgtcgggagc aagttcagca aaactcaaac ctttcagggt tgtggaatct gcagcctga     900
tccgcctgcc aacatcacag tcactgccgt ggccagaaac cccgctggc tcagtgtcac     960
ctggcaagac ccccactcct ggaactcatc tttctacaga ctacggtttg agctcagata    1020
tcgggctgaa cggtcaaaga cattcacaac atggatggtc aaggacctcc agcatcactg    1080
tgtcatccac gacgcctgga cggcctgag gcacgtggtg cagcttcgtg cccaggagga    1140
gttcgggcaa ggcgagtgga gcgagtggag cccggaggcc atgggcacgc cttggacaga    1200
atccaggagt cctccagctg agaacgaggt gtccacccc atgcaggcac ttactactaa    1260
taaagacgat gataatattc tcttcagaga ttctgcaaat gcgacaagcc tcccagtgca    1320
agattcttct tcagtaccac tgcccacatt cctggttgct ggagggagcc tggccttcgg    1380
aacgctcctc tgcattgcca ttgttctgag gttcaagaag acgtggaagc tgcgggctct    1440
gaaggaaggc aagacaagca tgcatccgcc gtactctttg gggcagctgg tcccggagag    1500
gcctcgaccc accccagtgc ttgttcctct catctcccca ccggtgtccc ccagcagcct    1560
ggggtctgac aatacctcga gccacaaccg accagatgcc agggacccac ggagcccta    1620
tgacatcagc aatacagact acttcttccc cagatagctg gctgggtggc accagcagcc    1680
tggaccctgt ggatgataaa acacaaacgg gctcagca                           1718
```

<210> SEQ ID NO 13
<211> LENGTH: 456
<212> TYPE: DNA
<213> ORGANISM: Artificial Sequence
<220> FEATURE:
<223> OTHER INFORMATION: Consensus sequence of human gp80 and cyno gp80.

<400> SEQUENCE: 13

```
Met Leu Ala Val Gly Cys Ala Leu Leu Ala Leu Leu Ala Pro Gly
  1               5                  10                  15

Ala Ala Leu Ala Pro Cys Pro Ala Gln Glu Val Ala Arg Gly Val Leu
            20                  25                  30

Thr Ser Leu Pro Gly Asp Ser Val Thr Leu Thr Cys Pro Gly Glu Pro
        35                  40                  45

Glu Asp Asn Ala Thr Val His Trp Val Leu Arg Lys Pro Ala Gly Ser
    50                  55                  60

His Ser Arg Trp Ala Gly Met Gly Arg Arg Leu Leu Leu Arg Ser Val
65                  70                  75                  80

Gln Leu His Asp Ser Gly Asn Tyr Ser Cys Tyr Arg Ala Gly Arg Pro
                85                  90                  95

Ala Ala Thr Val His Leu Leu Val Asp Val Pro Glu Glu Pro Gln
            100                 105                 110

Leu Ser Cys Phe Arg Lys Ser Pro Leu Ser Asn Val Val Cys Glu Trp
            115                 120                 125

Gly Pro Arg Ser Thr Pro Ser Thr Thr Lys Ala Val Leu Leu Val Arg
    130                 135                 140

Lys Phe Gln Asn Ser Pro Ala Glu Asp Phe Gln Glu Pro Cys Gln Tyr
145                 150                 155                 160

Ser Gln Glu Ser Gln Lys Phe Ser Cys Gln Leu Ala Val Pro Glu Gly
                165                 170                 175

Asp Ser Ser Phe Tyr Ile Val Ser Met Cys Val Ala Ser Ser Val Gly
            180                 185                 190

Ser Lys Ser Lys Thr Gln Thr Phe Gln Gly Cys Gly Ile Leu Gln Pro
    195                 200                 205

Asp Pro Pro Ala Asn Ile Thr Val Thr Ala Val Ala Arg Asn Pro Arg
210                 215                 220

Trp Leu Ser Val Thr Trp Gln Asp Pro His Ser Trp Asn Ser Ser Phe
225                 230                 235                 240

Tyr Arg Leu Arg Phe Glu Leu Arg Tyr Arg Ala Glu Arg Ser Lys Thr
                245                 250                 255

Phe Thr Thr Trp Met Val Lys Asp Leu Gln His His Cys Val Ile His
            260                 265                 270

Asp Ala Trp Ser Gly Leu Arg His Val Val Gln Leu Arg Ala Gln Glu
    275                 280                 285

Glu Phe Gly Gln Gly Glu Trp Ser Glu Trp Ser Pro Glu Ala Met Gly
290                 295                 300

Thr Pro Trp Thr Glu Ser Arg Ser Pro Ala Glu Asn Glu Val Ser
305                 310                 315                 320

Thr Pro Gln Ala Thr Thr Asn Lys Asp Asp Asn Ile Leu Asp Ser
                325                 330                 335

Ala Asn Ala Thr Ser Leu Pro Val Gln Asp Ser Ser Ser Val Pro Leu
            340                 345                 350

Pro Thr Phe Leu Val Ala Gly Gly Ser Leu Ala Phe Gly Thr Leu Leu
    355                 360                 365

Cys Ile Ala Ile Val Leu Arg Phe Lys Lys Thr Trp Lys Leu Arg Ala
370                 375                 380

Leu Lys Glu Gly Lys Thr Ser Met His Pro Pro Tyr Ser Leu Gly Gln
385                 390                 395                 400

Leu Val Pro Glu Arg Pro Arg Pro Thr Pro Val Leu Val Pro Leu Ile
                405                 410                 415

Ser Pro Pro Val Ser Pro Ser Ser Leu Gly Ser Asp Asn Thr Ser Ser
```

```
                    420                 425                 430
His Asn Arg Pro Asp Ala Arg Asp Pro Arg Ser Pro Tyr Asp Ile Ser
            435                 440                 445

Asn Thr Asp Tyr Phe Phe Pro Arg
    450                 455
```